United States Patent
Welgus et al.

(10) Patent No.: US 12,233,042 B2
(45) Date of Patent: *Feb. 25, 2025

(54) TREATMENT OF CUTANEOUS DISORDERS

(71) Applicant: Verrica Pharmaceuticals Inc., West Chester, PA (US)

(72) Inventors: Howard Welgus, West Chester, PA (US); Matthew Gene Davidson, Venice, CA (US); Jayson Michael Rieger, Charlottesville, VA (US)

(73) Assignee: Verrica Pharmaceuticals Inc., West Chester, PA (US)

( * ) Notice: Subject to any disclaimer, the term of this patent is extended or adjusted under 35 U.S.C. 154(b) by 165 days.

This patent is subject to a terminal disclaimer.

(21) Appl. No.: 17/471,853

(22) Filed: Sep. 10, 2021

(65) Prior Publication Data

US 2021/0401793 A1 Dec. 30, 2021

Related U.S. Application Data

(63) Continuation of application No. 16/619,675, filed as application No. PCT/US2018/036353 on Jun. 6, 2018, now Pat. No. 11,147,790.

(60) Provisional application No. 62/516,061, filed on Jun. 6, 2017.

(51) Int. Cl.
  A61K 31/343 (2006.01)
  A61K 9/00 (2006.01)
  A61K 31/05 (2006.01)
  A61K 31/121 (2006.01)
  A61K 31/245 (2006.01)

(52) U.S. Cl.
  CPC ............ A61K 31/343 (2013.01); A61K 31/05 (2013.01); A61K 31/121 (2013.01); A61K 31/245 (2013.01); *A61K 9/0014* (2013.01)

(58) Field of Classification Search
  CPC .... A61K 31/05; A61K 31/121; A61K 31/245; A61K 31/343; A61K 9/0014
  See application file for complete search history.

(56) References Cited

U.S. PATENT DOCUMENTS

| | | |
|---|---|---|
| 600,556 A | 3/1898 | Schupphaus |
| 1,744,893 A | 1/1930 | Hein |
| 3,393,962 A | 7/1968 | Maurice |
| 3,981,924 A | 9/1976 | Hall |
| 4,143,050 A | 3/1979 | Rossy et al. |
| 4,148,874 A | 4/1979 | Smith |
| 4,157,967 A | 6/1979 | Meyst et al. |
| 4,298,752 A | 11/1981 | Dauben et al. |
| 4,299,006 A | 11/1981 | Cruz |
| 4,413,154 A | 11/1983 | Dessau |
| 4,895,727 A | 1/1990 | Allen |
| 5,445,462 A | 8/1995 | Johnson et al. |
| 5,464,855 A | 11/1995 | Capiris et al. |
| 5,590,780 A | 1/1997 | O'Meara |
| 5,702,694 A | 12/1997 | Chamness |
| 5,727,892 A | 3/1998 | Baudin |
| 6,066,124 A | 5/2000 | Caillouette |
| D436,661 S | 1/2001 | Berry |
| 6,379,342 B1 | 4/2002 | Levinson |
| 6,547,467 B2 | 4/2003 | Quintero |
| 6,673,031 B2 | 1/2004 | Mark |
| 6,811,342 B2 | 11/2004 | Pauchet |
| 8,518,076 B2 | 8/2013 | Stenton |
| 8,871,801 B2 | 10/2014 | Levitt |
| D771,250 S | 11/2016 | Zhang et al. |
| D772,407 S | 11/2016 | Zhang et al. |
| 9,480,691 B1 | 11/2016 | Roth |
| D801,830 S | 11/2017 | Zhang et al. |
| 10,195,635 B2 | 2/2019 | Sporrer |
| D868,160 S | 11/2019 | Lam |
| 10,745,413 B2 | 8/2020 | Davidson et al. |

(Continued)

FOREIGN PATENT DOCUMENTS

| | | |
|---|---|---|
| CH | 204207 A | 4/1939 |
| CN | 1571795 A | 1/2005 |

(Continued)

OTHER PUBLICATIONS

Extended European Search Report, mailed Mar. 10, 2017, in connection with EP 14837297.2.
International Search Report and Written Opinion, mailed Nov. 20, 2014, in connection with PCT/US2014/052184.
International Preliminary Report on Patentability, mailed Mar. 3, 2016, in connection with PCT/US2014/052184.
Extended European Search Report, mailed Oct. 26, 2018, in connection with EP 15871116.8.
International Search Report and Written Opinion, mailed Jul. 14, 2016, in connection with PCT/US2015/066487.

(Continued)

Primary Examiner — Umamaheswari Ramachandran
(74) Attorney, Agent, or Firm — Wolf, Greenfield & Sacks, P.C.

(57) ABSTRACT

Methods of treating one or more skin lesions using cantharidin as well as associated compositions, treatment regimens, kits, devices, and systems are provided. A method of treating a subject having one or more skin lesions may involve administering a composition comprising cantharidin to one or more skin lesions. The method may allow for the efficacious treatment of the skin lesion(s) with minimal or no adverse side effects (e.g., severe adverse side effects, permanent damage of the dermal tissue, scarring, excessive blistering of skin surrounding the lesion, elevated plasma cantharidin concentration, systemic exposure to cantharidin). The efficacy and/or safety of the treatment may be due, to certain features of the composition and/or prolonged exposure of the skin lesion(s) to cantharidin. The methods described herein may be used for a wide variety of cutaneous disorders, including skin disorders that primarily affect the epidermis of skin.

20 Claims, No Drawings

(56) References Cited

U.S. PATENT DOCUMENTS

| | | | |
|---|---|---|---|
| D900,312 S | 10/2020 | Davidson et al. | |
| 11,052,064 B2 | 7/2021 | Davidson | |
| D933,494 S | 10/2021 | Tempfli et al. | |
| 11,147,790 B2 | 10/2021 | Welgus et al. | |
| 11,168,091 B2 | 11/2021 | Davidson et al. | |
| D938,587 S | 12/2021 | Fujii et al. | |
| D947,027 S | 3/2022 | Marik | |
| 11,279,165 B2 | 3/2022 | Skinner et al. | |
| D957,625 S | 7/2022 | Reynolds | |
| 11,559,294 B2 | 1/2023 | Pollack et al. | |
| D1,036,656 S | 7/2024 | Davidson et al. | |
| 2003/0068331 A1 | 4/2003 | Battaglia et al. | |
| 2003/0072814 A1 | 4/2003 | Maibach et al. | |
| 2004/0011830 A1 | 1/2004 | Kim | |
| 2004/0152766 A1 | 8/2004 | Au-Yeung et al. | |
| 2004/0162533 A1 | 8/2004 | Alley | |
| 2004/0254561 A1 | 12/2004 | Stenton | |
| 2005/0019418 A1* | 1/2005 | Crutchfield | A61K 31/365 424/773 |
| 2005/0111900 A1 | 5/2005 | Fazzolari et al. | |
| 2005/0169696 A1 | 8/2005 | Albisetti | |
| 2006/0110415 A1 | 5/2006 | Gupta | |
| 2006/0116649 A1 | 6/2006 | Hagele | |
| 2006/0180613 A1 | 8/2006 | Manesis | |
| 2007/0000566 A1 | 1/2007 | Gueret | |
| 2007/0111954 A1 | 5/2007 | Crutchfield et al. | |
| 2007/0187437 A1 | 8/2007 | Lord | |
| 2007/0233020 A1 | 10/2007 | Hearne | |
| 2007/0233021 A1 | 10/2007 | Poisson et al. | |
| 2007/0275045 A1 | 11/2007 | Evans et al. | |
| 2008/0146674 A1 | 6/2008 | Rosenberg et al. | |
| 2008/0195040 A1 | 8/2008 | Clark et al. | |
| 2008/0246380 A1 | 10/2008 | Gwak | |
| 2009/0311028 A1 | 12/2009 | Odermatt et al. | |
| 2011/0086109 A1 | 4/2011 | Dever | |
| 2011/0208136 A1 | 8/2011 | Sollingen et al. | |
| 2011/0212033 A1 | 9/2011 | Tamarkin et al. | |
| 2012/0016320 A1 | 1/2012 | Lin | |
| 2012/0077784 A1 | 3/2012 | Whitbourne | |
| 2012/0148520 A1 | 6/2012 | Strobel et al. | |
| 2012/0190658 A1 | 7/2012 | Studin | |
| 2012/0312709 A1 | 12/2012 | Kaufman | |
| 2013/0004230 A1 | 1/2013 | Kirk et al. | |
| 2013/0085137 A1 | 4/2013 | Grigorian et al. | |
| 2013/0197075 A1 | 8/2013 | Levitt | |
| 2014/0275248 A1 | 9/2014 | Johnson | |
| 2015/0118164 A1 | 4/2015 | Tamarkin et al. | |
| 2015/0328259 A1 | 11/2015 | Shanler et al. | |
| 2016/0193177 A1 | 7/2016 | Davidson | |
| 2017/0305925 A1 | 10/2017 | Piotrowski et al. | |
| 2019/0002474 A1 | 1/2019 | Davidson et al. | |
| 2019/0031674 A1 | 1/2019 | Davidson et al. | |
| 2020/0155498 A1 | 5/2020 | Welgus et al. | |
| 2020/0270269 A1 | 8/2020 | Davidson et al. | |
| 2021/0070771 A1 | 3/2021 | Davidson et al. | |
| 2021/0138214 A1 | 5/2021 | Davidson et al. | |
| 2021/0386703 A1 | 12/2021 | Davidson | |
| 2024/0109911 A1 | 4/2024 | Davidson et al. | |

FOREIGN PATENT DOCUMENTS

| | | |
|---|---|---|
| CN | 1966508 A | 5/2007 |
| CN | 101012230 A | 8/2007 |
| CN | 101108853 A | 1/2008 |
| CN | 101108854 A | 1/2008 |
| CN | 101161654 A | 4/2008 |
| CN | 101453923 A | 6/2009 |
| CN | 101108853 B | 5/2010 |
| CN | 101798309 A | 8/2010 |
| CN | 101036774 B | 12/2010 |
| CN | 102146086 A | 8/2011 |
| CN | 102268006 A | 12/2011 |
| CN | 102336765 A | 2/2012 |
| CN | 102526146 A | 7/2012 |
| CN | 202730045 A | 2/2013 |
| CN | 202920809 U | 5/2013 |
| CN | 102268006 B | 8/2013 |
| CN | 103923095 A | 7/2014 |
| CN | 204817029 U | 12/2015 |
| CN | 105636637 A | 6/2016 |
| CN | 106674248 A | 5/2017 |
| DE | 20016131 U1 | 11/2000 |
| EP | 0841059 A1 | 5/1998 |
| GB | 587994 A | 5/1947 |
| JP | S51-141863 A | 12/1976 |
| JP | H3-202002 A | 9/1991 |
| JP | 05-058914 | 3/1993 |
| JP | H05-255367 A | 10/1993 |
| JP | H07-500980 A | 2/1995 |
| JP | 10-114626 A | 5/1998 |
| JP | 11-319064 | 11/1999 |
| JP | 11-335303 | 12/1999 |
| JP | 2004-059446 A | 2/2004 |
| JP | 2005-187330 A | 7/2005 |
| JP | 2007-269693 A | 10/2007 |
| JP | 2008-505960 A | 2/2008 |
| JP | 2010-516410 A | 5/2010 |
| JP | 2010-235471 A | 10/2010 |
| JP | 47-39621 B2 | 8/2011 |
| JP | 2001-245964 A | 9/2011 |
| JP | 2012-97152 A | 5/2012 |
| JP | 2013-507367 A | 3/2013 |
| JP | 2016-528015 A | 9/2016 |
| JP | 2017-513907 A | 6/2017 |
| KR | 10-2005-0032154 A | 4/2005 |
| KR | 100786203 B1 | 12/2007 |
| KR | 10-2016-0045086 A | 4/2016 |
| KR | 10-2017-0029413 A | 3/2017 |
| WO | WO 2008/092068 A2 | 7/2008 |
| WO | WO 2010/002476 A1 | 1/2010 |
| WO | WO 2010/079513 A2 | 7/2010 |
| WO | WO 2011/035019 A1 | 3/2011 |
| WO | WO 2012/131238 A1 | 10/2012 |
| WO | WO 2013/189841 A1 | 12/2013 |
| WO | WO 2015/027111 A1 | 2/2015 |
| WO | WO 2016/006693 A1 | 1/2016 |
| WO | WO 2016/100732 A2 | 6/2016 |
| WO | WO 2016/118633 A1 | 7/2016 |
| WO | WO 2016/134130 A1 | 8/2016 |
| WO | WO 2018/226894 A1 | 12/2018 |

OTHER PUBLICATIONS

International Preliminary Report on Patentability, mailed Jun. 29, 2017, in connection with PCT/US2015/066487.

Supplementary European Search Report, mailed Aug. 8, 2018, in connection with EP 16740681.8.

Extended European Search Report, mailed Dec. 4, 2018, in connection with EP 16740681.8.

International Search Report and Written Opinion, mailed Jul. 1, 2016, in connection with PCT/US2016/014139.

International Preliminary Report on Patentability, mailed Aug. 3, 2017, in connection with PCT/US2016/014139.

Extended European Search Report, mailed Feb. 2, 2021, in connection with EP 18813599.0.

Invitation to Pay Additional Fees, mailed Aug. 27, 2018, in connection with PCT/US2018/O3653.

International Search Report and Written Opinion, mailed Oct. 22, 2018, in connection with PCT/US2018/036353.

International Preliminary Report on Patentability, mailed Dec. 19, 2019, in connection with PCT/US2018/036353.

Invitation to Pay Additional Fees, mailed Sep. 20, 2018, in connection with PCT/US2018/037808.

International Search Report and Written Opinion, mailed Nov. 13, 2018, in connection with PCT/US2018/037808.

International Preliminary Report on Patentability mailed Dec. 26, 2019 in connection with International Application No. PCT/US2018/037808.

Partial Supplementary European Search Report for Application No. EP 18864069.2, mailed Apr. 12, 2021.

(56) References Cited

OTHER PUBLICATIONS

Extended European Search Report for Application No. EP 18864069. 2, mailed Jul. 7, 2021.
Invitation to Pay Additional Fees, mailed Dec. 10, 2018, in connection with PCT/US2018/054373.
International Search Report and Written Opinion, mailed Apr. 3, 2019 in connection with PCT/US2018/054373.
International Preliminary Report on Patentability mailed Apr. 16, 2020, in connection with International Application No. PCT/US2018/054373.
[No Author Listed] CAS RN 27607-77-8. Entered STN: Nov. 1, 19846. 28 pages.
[No Author Listed] CAS RN 76262-87-8. Entered STN: Nov. 1, 19846. 19 pages.
[No Author Listed] CAS RN 89672-77-5. Entered STN: Nov. 1, 19846. 29 pages.
[No Author Listed] Dormer Laboratories, "Cantharone and Cantharone Plus" sales brochure. Publication date unknown.
Aitken et al., Fragmentation patterns in the gas-phase pyrolysis of some bi- and tri-cyclic sulfolanes related to the 8-thiabicyclo[4.3.0]non-3-ene 8,8-dioxide ring system . J Chem Soc. Perkin Transactions 1. 1994;16:2301-2308.
Anderson et al., Practical Process Research and Development. 1st Edition. Academic Press. Mar. 20, 2000. 81-111.
Aono et al., New method for generation of thiocarbonyl ylides from bis(trimethylsilylmethyl) sulfoxides and their application to cycloadditions. Heterocycles. 1995;40(1):249-60.
Augé et al., Catalysis by Lithium Cation: Lithium Trifluoromethanesulfonate as a Substitute for Lithium Perchlorate in Cycloadditions. Synlett 2000;6:877-9.
Bagatell, Studies On Biological Factors In Acantholysis. J Invest Dermatol. Nov. 1964;43:357-61.
Baker et al., Biotin; the structure of 2-alkyldihydrothiophene-3,4-dicarboxylic acids. J Org Chem. Jan. 1948;13(1):123-33. doi: 10.1021/jo01159a017.
Bouacha et al., A theoretical study of the mechanism, stereoselectivity and Lewis acid catalyst on the Diels-Alder cycloaddition between furan and activated alkenes. Tetrahedron Letters. 2013;54:4030-4033.
Braddock et al., Stereochemistry of the Catalysed Diels-Alder Reaction between Cyclopentadiene and Dimethyl Monothionofumarate; Soft versus Hard Lewis Acids. J. Chem. Soc. Chem. Commun. Jan. 1, 1993;16:1244-6. doi: https://doi.org/10.1039/C39930001244.
Brion et al., On the lewis acid catalyzed diels-alder reaction of furan. regio- and stereospecific synthesis of substituted cyclohexenols and cyclohexadienols. Tetrahedron Letters. 1982;23(50):5299-302. https://doi.org/10.1016/S0040-4039(00)85823-2.
Cacchi et al., Palladium-catalyzed carbonylation of enol triflates. A novel method for one-carbon homologation of ketones to ?,?-unsaturated carboxylic acid derivatives. Tetrahedron Letters. 26(8), 1985, pp. 1109-1112.
Chung et al., Sequential Nitromethane Conjugate Addition/Elimination—PD-Catlyzed Allylation of beta-Trifloxy Acrylates. Application to Carbapenem Synthesis. Org Lett. 1999;1(11):1783-1785.
Dang et al., Determination of trace cantharidin in plasma and pharmacokinetic study in beagle dogs using gas chromatography-mass spectrometry. J Anal Toxicol. Sep. 2009;33(7):384-8.
Dauben et al., Organic reactions at high pressure. Cycloadditions with furans. J. Am. Chem. Soc. 1976;98(7):1992-1993.
Dauben et al., Organic reactions at high pressure. The preparative scale synthesis of cantharidin. J. Org. Chem. 1985;50 (14):2576-2578.
Dauben et al., Simple, efficient total synthesis of cantharidin via a high-pressure Diels-Alder reaction. J. Am. Chem. Soc. 1980;102(22):6893-6894.

Gaul, Part I. Diels-Alder reactions performed in highly polar media. Part II. Reactions of allenylstannanes with in situ generated immonium ions. Dissertation. Indiana University, Bloomington Indian, 1990. 152 pages.
Grieco et al., Dramatic rate accelerations of Diels-Alder reactions in 5 M lithium perchlorate-diethyl ether: the cantharidin problem reexamined. J. Am. Chem. Soc. 1990;112(11):4595-4596.
Handy et al., Lithium Trifluoromethanesulfonimide in Acetone Or Diethyl-ether As a Safe Alternative To Lithium Perchlorate in Diethyl-ether for Effecting Diels-alder Reactions. Unexpected Influence of the Counterion On Exo/endo Selectivity. Synlett 1995;5:565-567.
Hollis et al., Homogeneous catalysis. Titanium complex [Ti(Cp)2(CF3SO3)2] and zirconium complex [Zr(Cp)2(CF3SO3)2THF], efficient catalysts for the Diels-Alder reaction. Organometallics. Aug. 1, 1992;11(8):2745-8. https://doi.org/10.1021/om00044a004.
Hollis et al., Homogenous Catalysis: Transition Metal Based Lewis Acid Catalysts. Tetrahedron. 1993;49(25):5415-30. doi: https://doi.org/10.1016/S0040-4020(01)87259-8.
Houk et al, On Lewis Acid catalysis of diels-alder reactions. J Am Chem Soc. Jun. 13, 1973;95(12):4094-4096.
Huang, Catalysts for Hetero Diels-Alder Reaction of Imines. Chinese Journal of Organic Chemistry. Oct. 2003;23(10):1064-75.
Hubbard et al., Lewis Acid Catalyzed Diels?Alder Reactions of Highly Hindered Dienophiles. J. Org. Chem. 1998;63(12):4143-4146.
Hunt et al., Why do catalytic quantities of lewis acid generally yield more product than 1.1 equiv in the intramolecular diels-adler reaction with a furan diene? Competitive complexation NMR studies provide an answer. J Am Chem Soc. 1995;117:1049-1056.
Kharitonov et al., Synthetic transformations of higher terpenoids: VIII. [4+2]-Cycloaddition reactions of lambertianic acid. Russian J Organic Chem. 2003;39(1):57-74.
Kronemyer et al., Verrica develops a solution for common warts. Retrieved from www.dermatologytimes.com. Nov. 13, 2017. 1 page.
Lange et al., Synthesis of 4-carboxy-2-thiabicyclo [3.2.0] Heptan-6-ones via 3-carboxy-2,3-dihydrothiophenes: potential ?-lactamase inhibitors. Tetrahedron Lett. 1985;26(15):1791-1794.
Magyarosy et al., Cycloaddition approach to the curing of polyimides via precursor containing thiophene-S,S-dioxide. Hetero Chem. 2006;17(7):648-652.
Mehdinia et al., Analysis of cantharidin in false blister beetles (Coleoptera: Oedemeridae) by headspace solid-phase microextraction and gas chromatography-mass spectrometry. J Chromatogr B Analyt Technol Biomed Life Sci. Oct. 1, 2011;879(27):2897-901. doi:10.1016/j.jchromb.2011.08.020. Epub Aug. 22, 2011.
Moed et al., Cantharidin revisited: a blistering defense of an ancient medicine. Arch Dermatol. Oct. 2001;137(10):1357-60. doi: 10.1001/archderm.137.10.1357.
Nikbakhtzadeh et al., Origin, transfer and distribution of cantharidin-related compounds in the blister beetle *Hycleus scabiosae*. J Venom Animals Toxins. 2012;18(1):88-96.
Opposition to Patent Application No. 252907 by Wavelength Enterprises, Ltd., filed Mar. 1, 2021. 78 pages.
Pagni et al., A chemical, spectroscopic, and theoretical assessment of the lewis acidity of LiClO4 in Diethyl Ether. J. Org Chem. 1993;58:3130-3133.
Prabhakar Reddy et al., Synthesis, cytotoxic activity and structure-activity relationships of hedychenone analogues. Bioorg Med Chem Lett. Apr. 15, 2010;20(8):2525-8. doi: 10.1016/j.bmcl.2010.02.101. Epub Mar. 3, 2010.
Rosenberg et al., Cantharidin treatment of warts at home. Arch Dermatol. Aug. 1977;113(8):1134.
Rossy et al., Aromatization of Dihyrothiophenes. Thiophenesaccharin: A Sweet Surprise. J Org Chem. 1980;45:617-620.
Rudo et al., Cantharidin—als Potenzmittel entzaubert, aber Oct. 1, 2013. Chemie in Unserer Zeit. vol. 47, Issue 5. pp. 310-316. With Supporting Information.
Schenck et al., Ausfuhrliche Mitteilung erfolgt an anderer Stelle. Naturwissenshaften Oct. 15, 1953; 40: 581.

(56) References Cited

OTHER PUBLICATIONS

Song et al., Ionic liquids as powerful media in scandium triflate catalysed Diels-Alder reactions: significant rate acceleration, selectivity improvement and easy recycling of catalyst. Chem Commun. 2001;12:1122-3.

Sperry et al., Studies on the Diels-Alder reaction of annulated furans: application to the synthesis of substituted phenanthrenes. Tetrahedron Letters. Apr. 18, 2005;46(16):2789-93. Doi: 10.1016/j.tetlet.2005.02.148.

Stork et al., A Stereospecific Synthesis of Cantharidin. J. Am. Chem. Soc., 1953;75(2):384-392.

Stork et al., Cantharidin. A Stereospecific Total Synthesis. J. Am. Chem. Soc. 1951;73(9):4501-4501.

Terao et al., Thiocarbonyl Ylides. VI. New Generation of Thiocarbonyl Ylides from Organosilicon Compounds Containing Sulfur and Their 1, 3-Cycloadditions. J-STAGE. 1987;35(5):1734-1740.

Torbeck et al., Cantharidin: a comprehensive review of the clinical literature. Dermatol Online J. Jun. 15, 2014;20(6):13030/qt45r512w0.

Tseng et al., Synthesis and Evaluation of Cantharidinimides on Human Cancer Cells. J Exp Clin Med. Oct. 2012;4(5):280-283.

Verma et al., Bioactive component, cantharidin from Mylabris cichorii and its antitumor activity against Ehrlich ascites carcinoma. Cell Biol Toxicol. Jun. 2012;28(3):133-47. doi: 10.1007/s10565-011-9206-6. Epub Mar. 9, 2012.

White et al., Dihydrothiophenes as precursors to fused quinolines, quinolones and coumarins via o-quinodimethane intermediates. Tetrahedron 52(9), Feb. 26, 1996, pp. 3117-3134.

White et al., Quinoline Analogues of Ortho-Quinodimethane. Tetrahedron Lett. 1995;36(33):5983-5986.

[No Author Listed] Journal of Organic Chemistry Author Guidelines. Last updated May 5, 2022. 3 pages.

Chen et al., Precautions with gentian violet: skin marking made sterile, effective, and economical. Am J Infect Control. Apr. 2009;37(3):244-6. doi: 10.1016/j.ajic.2008.06.005. Epub Oct. 14, 2008.

Earle et al., Diels-Alder reactions in ionic liquids. A safe recyclable alternative to lithium perchlorate-diethyl ether mixtures. Green Chem. Feb. 1999;1:23-25. doi: 10.1039/A808052F.

Gaines et al., Trimethylgallium. In: Inorganic Syntheses. Parshall, ed. Jan. 1, 1974. Retrieved from <https://onlinelibrary.wiley.com/doi/10.1002/9780470132463.ch45> on Apr. 12, 2023. 3 pages.

Harreus et al., 2-Pyrrolidone. Ullmann's Encyclopedia of Industrial Chemistry. 2000. doi: doi: 10.1002/14356007.a22_457.pub2.

Pulce et al., Denatonium Benzoate. Human Toxicol. Jan. 1996;1-12. Accessed Sep. 12, 2022 from <https://www.sciencedirect.com/topics/medicine-and-dentistry/denatonium-benzoate>.

Extended European Search Report, mailed Apr. 11, 2024 for European Application No. 24153182.1.

\* cited by examiner

TREATMENT OF CUTANEOUS DISORDERS

RELATED APPLICATIONS

This application is a continuation of and claims priority under 35 U.S.C. § 120 to U.S. Application, U.S. Ser. No. 16/619,675, filed Dec. 5, 2019, which is a national stage filing under 35 U.S.C. § 371 of international PCT application, PCT/US2018/036353, filed Jun. 6, 2018, which claims priority under 35 U.S.C. § 119(e) to U.S. Provisional Application, U.S. Ser. No. 62/516,061, filed Jun. 6, 2017, the entire contents of each of which are incorporated herein by reference.

BACKGROUND

Many cutaneous disorders produce lesions on the skin. Some of these lesions are in the form of epidermal growths on the skin. For instance, warts are small epidermal skin growths caused by viral infections, often found on the hands or feet. The most common type of wart is called Verruca vulgaris, which can be caused by multiple different strains of the Human papilloma virus (HPV). On most parts of the body these warts may be referred to as common warts; however, they may be referred to as plantar warts when on the feet or genital warts or condoloma when on the genitals. Other epidermal viral conditions such as *Molluscum contagiosum* resemble warts but are caused by distinct viruses. These viral mediated skin growths may be unsightly and may have a significant risk for cancerous transformation and for spreading, making their removal desirable. Other superficial hyper-proliferative disorders resemble warts but are caused by non-viral mechanisms and include seborrheic keratosis, actinic keratosis and porokeratosis.

Multiple modalities have been used to remove warts, *Molluscum contagiosum*, and other cutaneous diseases, including cryotherapy; surgical curettage; laser treatment; irritants such as salicylic acid and zinc oxide; acids such as nitric acid and squaric acid, immunotherapeutics such as imiquimod, 2,4-dinitrochlorobenzene and *Candida* antigen; and chemotherapeutics such as bleomyocin, podophyllotoxin and 5-fluorouracil. Many of these therapies can be painful, while others can leave disfiguring scars and/or require daily application. Perhaps most troubling, however, is that many of these cutaneous disorders remain recalcitrant even after multiple follow-up treatments. Accordingly, improved therapies are needed for treating these conditions.

SUMMARY

Methods of treating skin lesions (e.g., *Molluscum contagiosum*, seborrheic keratosis, actinic keratosis, milia, age spots, porokeratosis, or skin cancer) using cantharidin as well as associated compositions and devices are provided. The subject matter of the present invention involves, in some cases, interrelated products, alternative solutions to a particular problem, and/or a plurality of different uses of one or more systems and/or articles.

In general, the present disclosure provides cantharidin compositions for treating *Molluscum contagiosum* and other cutaneous diseases. A cantharidin composition can contain cantharidin, an intraepiderimal blistering agent. Methods utilizing the cantharidin compositions of the present disclosure can have many advantages over traditional therapies, including improved pharmacodynamics, improved safety, improved tolerability, minimal or no adverse side effects, and high single application efficacy. Advantages of the cantharidin composition, described herein, over previously used cantharidin compositions include the ability to be left on the skin for relatively long periods of time, improved safety, the removal of highly volatile and potentially explosive solvents (e.g., highly flammable solvents), compatibility with common plastics for ease of delivery, and improved biocompatibility.

Due to the nature of the solvents used in previously described cantharidin compositions, the application of cantharidin has been limited to screw top glass containers which have a number of limitations. Devices provided herein can be used for the precise application of a cantharidin formulation for the treatment of warts and *Molluscum contagiosum* topical indications.

One aspect of the present disclosure provides method of treating a subject having one or more skin lesions. The method may comprise administering a composition having improved properties relative to traditional cantharidin formulations. The treatment methods of the present disclosure may allow for cantharidin to be retained on the skin for longer periods of time than traditional treatment methods for certain skin disorders (e.g., surficial skin disorders, skin disorders not caused by HPV). For example, the method may comprise allowing the composition comprising cantharidin to remain on the skin lesion for greater than 6 hours (e.g., greater than or equal to 18 hours and less than or equal to about 24 hours). The treatment method of the present disclosure may have enhanced safety, efficacy, pharmacodynamics of cantharidin, and tolerability compared to traditional treatment methods. In some cases, the treatment method may have minimal or no adverse side effects. For example, the treatment method may not induce blistering on the skin surrounding the skin lesion and/or on normal tissue after extended exposure to the composition comprising cantharidin. The treatment method may result in a relatively high penetration of the cantharidin into the skin lesion. The treatment method may result in a relatively high percentage (e.g., all) of the treated skin lesions being removed after relatively few treatments (e.g., two, three, four).

Another aspect of the present disclosure provides for cantharidin compositions. The cantharidin may be dissolved or otherwise dispersed in a solvent (e.g., non-aqueous solvent). In some embodiments, the solvent in the composition may have an increased long-term stability and/or stability during use compared to solvents traditionally used in cantharidin composition, such as diethyl ether. In some such cases, the compositions, described herein, may be less susceptible to fluctuations in cantharidin concentration, e.g., due to solvent evaporation from the composition while stored in the device used to house or otherwise retain the composition for a period of time. The composition may comprise cantharidin and other excipients that allow a portion of the composition (e.g., composition absence a certain amount of solvent) to remain adhered to the skin lesion after administration. The composition may be firmly adhered to the skin of the subject and may remain adhered after normal activity by the subject for extended periods of time and minor exposure to water. The composition may be designed to allow for relatively high penetration of cantharidin into and retention of cantharidin within the skin lesion.

Another aspect of the present disclosure provides a kit for administering a cantharidin formulation to a subject. The kit can comprise a plurality of separately packaged, individually removable, dosage units in liquid or gel form. In some examples, a dosage unit is in a delivery device or system. In some cases, a dosage unit is in a packaging unit (e.g., ampule).

Another aspect of the present disclosure provides an applicator device for delivering a cantharidin formulation to a subject. The applicator unit can deliver the cantharidin formulation to the subject. The applicator device may be a single-use applicator.

Another aspect of the present disclosure provides instructions for the optimal treatment schedule. Different doses of cantharidin, the preparation of the skin, the frequency and quantity applied to the skin, how the skin is cared for after application and the amount of time cantharidin is left in contact with the skin have not been thoroughly tested by others and are not intuitively obvious to those skilled in the art as evidenced by the variability in peer-reviewed publications. The methods herein allow for the optimally effective treatment of *Molluscum contagiosum* and/or other cutaneous disorders with a cantharidin composition.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

DETAILED DESCRIPTION

Methods of treating one or more skin lesions using cantharidin as well as associated compositions, treatment regimens, kits, devices, and systems are provided. In some embodiments, a method of treating a subject having one or more skin lesions may involve administering a composition comprising cantharidin to the skin. For instance, the composition may be administered to one or more skin lesions (e.g., resulting from a *Molluscum contagiosum* infection) on the skin. The method may allow for the efficacious treatment (e.g., removal) of the skin lesion(s) with minimal or no adverse side effects (e.g., severe adverse side effects, permanent damage of the dermal tissue, scarring, excessive blistering of skin surrounding the lesion, elevated plasma cantharidin concentration, systemic exposure to cantharidin). The efficacy and/or safety of the treatment may be due to certain features of the composition and/or prolonged exposure of the skin lesion(s) to cantharidin. For instance, a relatively high percentage of the cantharidin administered to the skin lesion(s) may be retained on the skin lesion for a relatively long period of time (e.g., greater than 6 hours). In some embodiments, the composition comprising cantharidin that is administered to the skin may allow for localized delivery of the composition and therefore cantharidin to the skin lesion(s) (e.g., to prevent exposure of surrounding skin to the composition or cantharidin and/or to prevent systemic exposure to the composition or cantharidin), for relatively good adherence to the skin lesion(s), for relatively high penetration of cantharidin into the skin lesion(s) over time, and/or for use of a relatively low concentration (e.g., less than or equal to about 1.2% w/v) and/or pharmacodynamics of cantharidin. The methods described herein may be used for a wide variety of cutaneous disorders, including skin disorders that primarily affect the epidermis of skin. For example, the method may be used to treat *Molluscum contagiosum* infection, seborrheic keratosis, actinic keratosis, milia, skin cancer, age spots, and other disorders not caused by human papilloma virus.

Cantharidin is used as a blistering agent for the treatment of certain skin disorders. However, cantharidin is also classified as an extremely hazardous substance in the United States and may cause severe chemical burns as well as toxicity when ingested. Accordingly, cantharidin may cause adverse side effects (e.g., scarring) under certain conditions. For instance, historically, certain adverse effects, such as damage of the dermal tissue, blistering of normal skin surrounding the lesion, pain, and elevated plasma cantharidin concentration, have occurred during the treatment of certain skin disorders using cantharidin. Current best practices for the treatment of certain skin disorders using cantharidin include brief exposure (e.g., less than about 4 hours) of the lesion to cantharidin to prevent these adverse side effects (e.g., severe adverse side effects).

As described in the present disclosure, certain methods, compositions, and devices do not suffer from one or more limitations typically associated with cantharidin compositions and their use. For instance, certain treatment methods may expose the skin lesion(s) to cantharidin for a relatively long period of time (e.g., greater than 6 hours, greater than or equal to 12 hours, greater than or equal to about 18 hours, greater than or equal to about 6 hours and less than or equal to about 72 hours, greater than or equal to about 18 hours and less than or equal to about 24 hours) with minimal or no adverse side effects (e.g., severe adverse side effects).

In some embodiments, a method of treating a subject having a skin lesion may comprise administering (e.g., topically) a composition comprising cantharidin to the skin lesion. In certain embodiments, the composition may comprise a relatively low concentration of cantharidin (e.g., less than or equal to about 1.2% w/v, less than or equal to about 1% w/v, greater than or equal to about 0.5% w/v and less than or equal to about 1% w/v). The cantharidin may be dissolved or otherwise dispersed in a solvent (e.g., non-aqueous solvent). In some embodiments, the solvent in the composition may have an increased long-term stability and/or stability during use compared to solvents traditionally used in cantharidin composition, such as diethyl ether. In some such cases, the compositions, described herein, may be less susceptible to fluctuations in cantharidin concentration, e.g., due to solvent evaporation from the composition while stored in the device used to house or otherwise retain the composition for a period of time. For instance, the concentration of cantharidin in the device (e.g., applicator) may remain relatively constant over time and/or after several uses. In certain embodiments, the solvent in the composition is less volatile than solvents utilized in existing and/or traditional cantharidin compositions. In certain embodiments, the solvent has a vapor pressure of less than or equal to about 350 mm Hg (e.g., less than or equal to about 210 mm Hg) at 20° C. In some such cases, the solvent is an alcohol (e.g., ethanol) and acetone. In certain cases, the solvent is a non-ether solvent and/or does not comprise diethyl ether. In certain embodiments, the composition has a vapor pressure of less than or equal to about 210 mm Hg (e.g., less than or equal to about 126 mm Hg) at 20° C. In some cases, the composition comprises a relatively small weight percentage (e.g., less than or equal to about 20 wt. %, less than or equal to about 10 wt. %) of an ether, such as diethyl ether. In certain embodiments, the composition may comprise one or more components in addition to the cantharidin and a pharmaceutically acceptable excipient (e.g., solvent). For instance, the composition may comprise a film-forming agent (e.g., polymer, nitrocellulose and/or hydroxypropyl cellulose), a plasticizer (e.g., penetration enhancer, oil, camphor and/or castor oil), a dye (e.g., gentian violet), and/or a bittering agent (e.g., denatonium benzoate.). In certain embodiments, the viscosity of the composition may be less than 100 cps, less than 90 cps, less than 80 cps, less than 70 cps, less than 60 cps, less than 55 cps, more than 30 cps, more than 35 cps, about 30-100 cps, about 30-70 cps, about 35-60 cps or about 40-50 cps.

In some embodiments, the composition may be administered and/or the composition may be formulated such that a relatively large percentage of the composition does not spread outside the margins of the skin lesion being treated after administration (e.g., topical administration). In certain embodiments, the spread of the composition to at least a portion of the skin surrounding the lesion (e.g., normal tissue) may be minimized by delivering a certain volume to the skin lesion and/or through the use of certain applicators (e.g., precision applicator tips). In some embodiments, the composition may be formulated to allow for suitable coverage of the lesion while minimizing spread of the composition to the skin surrounding the lesion. Regardless of whether the composition spreads, the composition may result in minimal or no adverse side effects (e.g., severe adverse side effects).

In some embodiments, at least a portion of the composition may be allowed to remain on the skin lesion for a certain period of time (e.g., greater than 6 hours, greater than or equal to about 18 hours and less than or equal to about 24 hours). For example, at least some or substantially all of the solvent in the composition may evaporate leaving a material (e.g., film) on the skin (e.g., skin lesion). The material may comprise the cantharidin and a film-forming agent (e.g., nitrocellulose). In certain embodiments, the material may also comprise other components, such as a penetration enhancer, a dye, an aversive agent. In some embodiments, the remaining composition (e.g., portion of the composition remaining on the skin lesion) may have beneficial skin adhesion, flexibility, and/or safety (e.g., relatively low or no blister formation outside of the margins of the lesion) properties. For example, the remaining composition may form a film on the skin lesion. In certain embodiments, the film forms as a result of removal (e.g., via evaporation) of the solvent (e.g., substantially all) during and/or after the administration step. In some cases, the film may remain adhered to the skin lesion during normal activity by the subject and/or during minor exposure to water for a certain period of time (e.g., greater than about 6 hours, greater than about 8 hours, greater than about 12 hours, greater than about 18 hours, greater than about 24 hours, indefinitely). In certain cases, the film is relatively flexible. For instance, the film may remain relatively continuous with relatively few or no discontinuous regions during normal activity for a certain period of time. In such cases, the film may undergo minimal flaking and/or form few or no cracks during normal activity.

In some embodiments, the remaining composition may be safe. In some such cases, the composition may not induce a blister on the skin surrounding the skin lesion within about 12 or more hours (e.g., about 24 or more hours) after the administration of the composition comprising cantharidin. For example, the composition may not result in blister formation (e.g., blistering) at distance of at least about 2 mm (e.g., about 5 mm, about 10 mm, about 15 mm, about 20 mm, about 30 mm) from the margin of the skin lesion within at least 6 hours (e.g., at least about 12 hours, at least about 24 hours) after the administration step and/or after continuous contact with the composition. As another example, the composition may not cause blisters outside of the margins of the skin lesion and/or the location of administration at least 6 hours (e.g., at least about 12 hours, at least about 24 hours) after the administration step and/or after continuous contact with the composition. In some embodiments, the composition does not produce blisters having a diameter of greater than about 10 mm (e.g., about 15 mm, about 20 mm, about 25 mm, about 30 mm, about 40 mm, about 50 mm) at a certain distance (e.g., at least 1 mm, at least about 2 mm) from the margin of the skin lesion after at least 6 hours (e.g., at least about 12 hours, at least about 18 hours, at least about 24 hours) of continuous contact with the skin when a 5 mm droplet of the composition is administered to the skin. In some embodiments, the composition does not produce blisters having a diameter of greater than about 10 mm (e.g., about 15 mm, about 20 mm, about 25 mm, about 30 mm, about 40 mm, about 50 mm) at a certain distance (e.g., at least 1 mm, at least about 2 mm) from the margin of the skin lesion after at least 6 hours (e.g., at least about 12 hours, at least about 18 hours, at least about 24 hours) of continuous contact with the skin when a droplet of the composition having a volume of less than or equal to about 10 µL is administered to the skin, e.g., over a 5 mm diameter area on the skin.

As noted above, in some embodiments, at least a portion of the composition may be allowed to remain on the skin lesion for a certain period of time. In some embodiments, the composition may be allowed to remain on the skin lesion for greater than about 6 hours, greater than or equal to about 8 hours, greater than or equal to about 10 hours, greater than or equal to about 12 hours, greater than or equal to about 14 hours, greater than or equal to about 16 hours, greater than or equal to about 18 hours, greater than or equal to about 20 hours, greater than or equal to about 22 hours, greater than or equal to about 24 hours, greater than or equal to about 28 hours, greater than or equal to about 32 hours, greater than or equal to about 36 hours, greater than or equal to about 40 hours, greater than or equal to about 44 hours, greater than or equal to about 48 hours, greater than or equal to about 52 hours, greater than or equal to about 56 hours, greater than or equal to about 60 hours, greater than or equal to about 64 hours, or greater than or equal to about 68 hours. In some instances, the composition may be allowed to remain on the skin lesion for less than or equal to about 72 hours, less than or equal to about 68 hours, less than or equal to about 64 hours, less than or equal to about 60 hours, less than or equal to about 56 hours, less than or equal to about 52 hours, less than or equal to about 48 hours, less than or equal to about 44 hours, less than or equal to about 40 hours, less than or equal to about 36 hours, less than or equal to about 32 hours, less than or equal to about 28 hours, less than or equal to about 24 hours, less than or equal to about 22 hours, less than or equal to about 20 hours, less than or equal to about 18 hours, less than or equal to about 16 hours, less than or equal to about 14 hours, less than or equal to about 12 hours, less than or equal to about 10 hours, or less than or equal to about 8 hour. All combinations of the above-referenced ranges are possible. For example, the composition may be allowed to remain on the skin lesion for greater than about 6 hours and less than or equal to about 72 hours, greater than about 12 hours and less than or equal to about 72 hours, greater than about 18 hours and less than or equal to about 72 hours, greater than about 12 hours and less than or equal to about 48 hours, greater than about 18 hours and less than or equal to about 36 hours, or greater than about 18 hours and less than or equal to about 24 hours.

It should be understood that the phrases "on the skin", "on the skin lesion", "on the lesion", etc. with respect to the composition or any of its components (e.g., cantharidin) may refer to the composition or any of its components being on top of (e.g., outside of the skin), within (e.g., contained within one or more layers of the skin, contained with the skin, contained within the lesion), and/or below one or more layers of the skin (e.g., superficial layer of the skin lesion, epidermal layer of the skin lesion). In some embodiments, at least a portion of (e.g., substantially all of) the composition or any of its components may remain on top of the skin lesion. In some embodiments, at least a portion of (e.g., substantially all of) the composition or any of its components may remain within the skin lesion. In some embodiments, at least a portion of (e.g., substantially all of) the composition or any of its components may be below one or more layers of the skin (e.g., superficial layer of the skin lesion, epidermal layer of the skin lesion).

In some embodiments, at least a portion of the solvent (e.g., substantially all) is removed from the composition during and/or after the administration step. For instance, at least a portion of the solvent (e.g., substantially all) is removed from the composition (e.g., via evaporation) after the administration step. In some such embodiments, the remaining composition may form a film on at least a portion of the skin lesion. In some embodiments, the rate and/or total time for removal (e.g., evaporation) of the solvent (e.g., substantially all) from the composition may be selected to produce beneficial properties. For instance, the vapor pressure of the solvent and/or the composition may be selected to control the rate and/or total time for removal (e.g., evaporation) the solvent (e.g., substantially all) from the composition. In some embodiments, the total time for removal (e.g., via evaporation) of at least a portion of the solvent (e.g., greater than or equal to about 50%, greater than or equal to about 75%, greater than or equal to about 90%, greater than or equal to about 95%, greater than or equal to about 99%, 100%) from the composition may be less than or equal to about 60 seconds, less than or equal to about 55 seconds, less than or equal to about 50 seconds, less than or equal to about 45 seconds, less than or equal to about 40 seconds, less than or equal to about 35 seconds, less than or equal to about 30 seconds, less than or equal to about 25 seconds, or less than or equal to about 20 seconds. In some instances, the total time for removal (e.g., evaporation) of at least a portion of the solvent (e.g., greater than or equal to about 50%, greater than or equal to about 75%, greater than or equal to about 90%, greater than or equal to about 95%, greater than or equal to about 99%, 100%) from the composition may be greater than or equal to about 10 seconds, greater than or equal to about 15 seconds, greater than or equal to about 20 seconds, greater than or equal to about 25 seconds, greater than or equal to about 30 seconds, greater than or equal to about 35 seconds, greater than or equal to about 40 seconds, greater than or equal to about 45 seconds, or greater than or equal to about 50 seconds. All combinations of the above-referenced ranges are possible (e.g., greater than about 30 seconds and less than or equal to about 60 seconds). In general, the time for removal of a least a portion of the solvent from the composition may be slower than certain traditional cantharidin formulation, such as those comprising diethyl ether or a certain percentage of diethyl ether. In some embodiments, removal of at least a portion of the solvent (e.g., substantially all of the solvent) may occur through passive and/or active means.

In some embodiments, a relatively large percentage of cantharidin administered to the skin lesion may penetrate the skin lesion (e.g., the epidermis of the skin lesion). For instance, in some embodiments, after the administration step and/or being allowed to remain on the skin for a certain period of time (e.g., 6 hours or less, 12 hours or less, 18 hours or less), greater than or equal to about 10%, greater than or equal to about 20%, greater than or equal to about 30%, greater than or equal to about 40%, greater than or equal to about 50%, greater than or equal to about 60%, greater than or equal to about 70%, greater than or equal to about 80%, greater than or equal to about 90%, greater than or equal to about 95%, or greater than or equal to about 99% of the administered cantharidin may be absorbed into the tissue (e.g., epidermal tissue) of the skin lesion. Accordingly, the composition remaining on the skin (e.g., film) after a certain period of time may contain a relatively small percentage of the administered cantharidin. For instance, the composition remaining on the skin (e.g., film) may comprise less than or equal to about 75%, less than or equal to about 50%, less than or equal to about 40%, less than or equal to about 30%, less than or equal to about 20%, less than or equal to about 10%, less than or equal to about 5%, less than or equal to about 2%, less than or equal to about 1%, or less than or equal to about 0.5% of the administered cantharidin.

Regardless of the percentage of administered cantharidin that penetrates into the skin lesion, the plasma concentration (e.g., concentration at a single time point, concentration at all time points, maximum concentration) of cantharidin in the subject may be relatively low. For instance, the plasma concentration of cantharidin in a subject (e.g., at least some subjects, all subjects) may be less than or equal to about 30 ng/ml, less than or equal to about 25 ng/ml, less than or equal to about 20 ng/ml, less than or equal to about 15 ng/ml, less than or equal to about 10 ng/ml, less than or equal to about 8 ng/ml, less than or equal to about 5 ng/ml, less than or equal to about 4.8 ng/ml, less than or equal to about 4.5 ng/ml, less than or equal to about 4.3 ng/ml, less than or equal to about 4 ng/ml, less than or equal to about 3.8 ng/ml, less than or equal to about 3.5 ng/ml, less than or equal to about 3.3 ng/ml, less than or equal to about 3 ng/ml, less than or equal to about 2.8 ng/ml, less than or equal to about 2.5 ng/ml, less than or equal to about 2.3 ng/ml, less than or equal to about 2 ng/ml, less than or equal to about 1.8 ng/ml, less than or equal to about 1.5 ng/ml, less than or equal to about 1.3 ng/ml, less than or equal to about 1 ng/ml, less than or equal to about 0.8 ng/ml, less than or equal to about 0.5 ng/ml, less than or equal to about 0.3 ng/ml, or less than or equal to about 0.1 ng/ml at least 2 hours (e.g., at least 6 hours, at least 12 hours, at least 24 hours) after administration of the composition comprising cantharidin. For example, in embodiments in which the composition is applied to more than one skin lesions (e.g., 2 or more, 5 or more, 10 or more, 15 or more, 20 or more, 25 or more, 50 or more, 100 or more) and/or up to about 900 microliters or up to 200 mg (e.g., 170 mg) of the composition is applied to skin lesions on the subject, the plasma concentration may be less than or equal to about 3.3 ng/mL or less than or equal to about 2.5 ng/mL (e.g., less than or equal to about 1 ng/mL, less than or equal to about 0.5 ng/mL, less than or equal to about 0.1 ng/mL) at least 2 hours (e.g., 2 hours, 6 hours, 24 hours) after administration of the composition. As another example, in embodiments in which the composition is applied to more than one skin lesions (e.g., 2 or more, 5 or more, 10 or more, 15 or more, 20 or more, 25 or more, 50 or more, 100 or more) and/or up to 200 mg (e.g., 170 mg) of the composition is applied to skin lesions on the subject, the plasma concentration may be less than or equal to about 3.3 ng/mL or less than or equal to about 2.5 ng/mL (e.g., less than or equal to about 1 ng/mL, less than or equal to about 0.5 ng/mL, less than or equal to about 0.1 ng/mL) at least 2 hours (e.g., 2 hours, 6 hours, 24 hours) after administration of the composition.

In some embodiments, the plasma concentration (e.g., concentration at a single time point, concentration at all time points, maximum concentration) of cantharidin in the subject may be relatively low for a wide range of number of lesions, lesions per pound of body weight (i.e., lesions per pound), ages, body weights, total administered dosages, and/or genital involvement. For instance, the plasma concentration (e.g., concentration at a single time point, concentration at all time points, maximum concentration) may be less than or equal to about 3.3 ng/mL (e.g., less than or equal to about 2.5 ng/mL, less than or equal to about 2.5 ng/mL) at least about 2 hours (e.g., 2 hours±30 minutes, 6 hours±1 hour, 24 hours±3 hours) after administration of the composition when the composition is administered to at least 20, at least 30, at least 40, at least 50, at least 60, at least 70, at least 80, at least 90, at least 100, or at least 110 skin lesions. In some embodiments, the plasma concentration may be less than or equal to about 3.3 ng/mL (e.g., less than or equal to about 2.5 ng/mL, less than or equal to about 1 ng/mL) at least about 2 hours after administration of the composition when the lesions per pound of the subject is greater than or equal to about 0.001, greater than or equal to about 0.01, greater than or equal to about 0.1, greater than or equal to about 0.25, greater than or equal to about 0.5, greater than or equal to about 0.75, greater than or equal to about 1, greater than or equal to about 1.25, greater than or equal to about 1.75, greater than or equal to about 2, greater than or equal to about 2.25, greater than or equal to about 2.5, greater than or equal to about 2.75, or greater than or equal to about 3. For instance, the plasma concentration may be less than or equal to about 3.3 ng/mL (e.g., less than or equal to about 2.5 ng/mL, less than or equal to about 1 ng/mL) at least about 2 hours after administration of the composition in embodiments in which the lesions per pound of the subject is greater than or equal to about 0.001 and less than or equal to about 3 (e.g., greater than or equal to about 0.1 and less than or equal to about 2.5).

In some embodiments, the plasma concentration (e.g., concentration at a single time point, concentration at all time points, maximum concentration) may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of greater than or equal to about 0.1 milligrams (e.g., greater than or equal to about 0.25 mg, greater than or equal to about 0.5 mg, greater than or equal to about 0.75 mg, greater than or equal to about 1 mg, greater than or equal to about 1.5 mg, greater than or equal to about 2 mg, greater than or equal to about 2.5 mg, greater than or equal to about 3 mg, greater than or equal to about 3.5 mg, greater than or equal to about 4 mg, greater than or equal to about 4.5 mg) of the composition per pound of the subject. For instance, the plasma concentration may be less than or equal to about 3.3 ng/mL (e.g., less than or equal to about 2.5 ng/mL) at least about 2 hours after administration of greater than or equal to about 0.1 mg and less than or equal to about 6 mg (e.g., greater than or equal to about 0.5 mg and less than or equal to about 6 mg, greater than or equal to about 0.75 mg and less than or equal to about 5 mg) of the composition per pound of the subject.

In some embodiments, the plasma concentration (e.g., concentration at a single time point, concentration at all time points, maximum concentration) may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of greater than or equal to about 0.5 milligrams of the composition per lesion (e.g., greater than or equal to about 3 mg/lesion, greater than or equal to about 3.5 mg/lesion, greater than or equal to about 4 mg/lesion, greater than or equal to about 4.5 mg/lesion, greater than or equal to about 5 mg/lesion, greater than or equal to about 5.5 mg/lesion, greater than or equal to about 6 mg/lesion, greater than or equal to about 6.5 mg/lesion, greater than or equal to about 7 mg/lesion, greater than or equal to about 7.5 mg/lesion, greater than or equal to about 8 mg/lesion greater than or equal to about 8.5 mg/lesion, greater than or equal to about 9 mg/lesion, greater than or equal to about 9.5 mg/lesion). For instance, the plasma concentration may be less than or equal to about 3.3 ng/mL (e.g., less than or equal to about 2.5 ng/mL, less than or equal to about 1 ng/mL) at least about 2 hours after administration of greater than or equal to about 3 mg/lesion and less than or equal to about 10 mg/lesion of the composition to the subject.

In some embodiments, the plasma concentration (e.g., concentration at a single time point, concentration at all time points, maximum concentration) may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of greater than or equal to about 0.01 milligrams of cantharidin per lesion (e.g., greater than or equal to about 0.01 mg/lesion, greater than or equal to about 0.02 mg/lesion, greater than or equal to about 0.03 mg/lesion, greater than or equal to about 0.04 mg/lesion, greater than or equal to about 0.05 mg/lesion, greater than or equal to about 0.06 mg/lesion, greater than or equal to about 0.07 mg/lesion, greater than or equal to about 0.08 mg/lesion, greater than or equal to about 0.09 mg/lesion, greater than or equal to about 0.1 mg/lesion, greater than or equal to about 0.2 mg/lesion, greater than or equal to about 0.3 mg/lesion, greater than or equal to about 0.4 mg/lesion, greater than or equal to about 0.5 mg/lesion). For instance, the plasma concentration may be less than or equal to about 3.3 ng/mL (e.g., less than or equal to about 2.5 ng/mL, less than or equal to about 1 ng/mL) at least about 2 hours after administration of greater than or equal to about 0.01 mg/lesion and less than or equal to about 0.5 mg/lesion (e.g., greater than or equal to about 0.07 mg/lesion and less than or equal to about 0.1 mg/lesion) of cantharidin to the subject.

In some embodiments, the plasma concentration (e.g., concentration at a single time point, concentration at all time points, maximum concentration) of cantharidin in the subject may be relatively low even in subjects having a relatively low body weight and/or age. For instance, the plasma concentration may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of the composition in subjects having a body weight of less than or equal to about 200 lb., less than or equal to about 175 lb., less than or equal to about 150 lb., less than or equal to about 125 lb., less than or equal to about 100 lb., less than or equal to about 90 lb., less than or equal to about 80 lb., less than or equal to about 70 lb., less than or equal to about 60 lb., less than or equal to about 50 lb., less than or equal to about 40 lb., or less than or equal to about 30 lb. In some instances, the plasma concentration may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of the composition in subjects having an age of less than or equal to about 20 years, less than or equal to about 18 years, less than or equal to about 15 years, less than or equal to about 12 years, less than or equal to about 10 years, less than or equal to about 8 years, less than or equal to about 5 years, or less than or equal to about 3 years. In some embodiments, the plasma concentration may be less than or equal to about 3.3 ng/mL (e.g., less than or equal to about 2.5 ng/mL, less than or equal to about 1 ng/mL) at least about 2 hours (e.g., 2 hours±30 minutes, 6 hours±1 hour, 24 hours±3 hours) after administration of the composition in subjects having one or more skin lesions in the genital region.

In some embodiments, the method may comprise repeated administration of the composition. For instance, the method may comprise administering a second composition comprising cantharidin to at least a portion of the skin lesion. In certain embodiments, the second composition may have substantially the same percent (w/v) of cantharidin as the composition. In some instances, the second composition may be substantially the same as the first composition. In some embodiments, the second composition may be administered a certain period of time (e.g., greater than or equal to about 1 day, greater than or equal to about 3 days, greater than or equal to about 5 days, greater than or equal to about one week, greater than or equal to about 2 weeks, greater than or equal to about 3 weeks) after the administration of the first composition. For instance, the second composition may be administered greater than or equal to about 14 days and less than or equal to about 28 days (e.g., greater than or equal to about 17 days and less than or equal to about 25 days, greater than or equal to about 18 days and less than or equal to about 24 days, greater than or equal to about 19 days and less than or equal to about 23 days, greater than or equal to about 20 days and less than or equal to about 22 days, 21 days) after administration of the first composition. For instance, the second composition may be administered about 3 weeks after administration of the first composition.

In general, the administration step may be repeated any suitable number of times required to treat the skin disorder. For instance, the administration step may be repeated 2 or more, 3 or more, 4 or more, 5 or more, 6 or more, 7 or more, 8 or more, 9 or more, or 10 or more times. In certain embodiments, the total number of administration steps performed within a certain timeframe (e.g., 1 month, 2 months, 3 months, 4 months, 6 months, 8 months, 10 months, 12 months) and/or until a certain end point is reached (e.g., certain percent reduction in number of lesions, percent reduction in total volume of lesion(s)) may be greater than or equal to about 2 and less than or equal to about 10, greater than or equal to about 3 and less than or equal to about 10, greater than or equal to about 2 and less than or equal to about 8, greater than or equal to about 2 and less than or equal to about 6, or greater than or equal to about 3 and less than or equal to about 5. For example, the method may comprise performing two administration steps in a 6 week period of time. As another example, the method may comprise performing four administration steps in a 12 week period of time.

In some embodiments, the interval of time between each administration step (e.g., a first administration and a second administration) may be selected as desired. In some embodiments, the interval of time between at least some (e.g., each) administration step may be substantially the same. For instance, the time interval between at least some (e.g., each) administration step may be days (e.g., about 1 day, about 2 days, about 3 days, about 4 days, about 5 days, about 6 days), weeks (e.g., 1 week, 2 weeks, 3 weeks, 4 weeks), months (e.g., 1 month, 2 months, 3 months, 4 months, 5 months, 6 months, 7 months, 8 months, 9 months, 10 months, 11 months), or years (e.g., 1 year, 2 or more years). For example, the method may comprise administering a composition comprising cantharidin about every 3 weeks (e.g., every 21±4 days) for about 12 weeks. In certain embodiments, the interval of time between at least some (e.g., each) administration step may be different.

In some embodiments in which the administration step is repeated, the allowing step may also be repeated. In certain embodiments, the allowing step may be repeated after each administration. In some embodiments, the allowing step may be repeated after at least some but not all of the administration steps. In general, the repeated allowing step(s) may be as described herein.

In general, the treatment methods described herein may result in the separation of at least a portion of the epidermal tissue within the skin lesion from the dermal tissue without removing and/or damaging the dermal tissue. In some embodiments, the treatment methods described herein may have a relatively high efficacy. For instance, one or more administrations of the composition and/or allowing the composition to remain after one or more administrations may result in the removal of the skin lesion or substantial reduction of the volume of the lesion. In some embodiments in which more than one skin lesions is present on a subject and the composition is administered to at least some (e.g., substantially, each) of the lesions, a relatively high percentage (e.g., greater than or equal to about 90%, greater than or equal to about 95%, greater than or equal to about 99%, 100%) of the treated lesions may be removed and/or the total volume of the lesions may be reduced by a relatively high percentage (e.g., greater than or equal to about 50%, greater than or equal to about 60%, greater than or equal to about 75%, greater than or equal to about 90%, greater than or equal to about 99%, 100%). In some embodiments, the volume of a single skin lesion may be reduced by a relatively high percentage (e.g., greater than or equal to about 50%, greater than or equal to about 60%, greater than or equal to about 75%, greater than or equal to about 90%, greater than or equal to about 99%, 100%).

It should be understood that though the methods, compositions, and devices, described herein, can be used to treat one or more skin lesions on a subject caused by one or more skin disorders. Reference to a single skin lesion is for ease of explanation. In general, the methods, compositions, and devices, described herein, may be used to treat a plurality of skin lesions (e.g., 2 or more, 5 or more, 10 or more, 15 or more, 20 or more, 30 or more, 40 or more, 50 or more, 75 or more, 100 or more, 200 or more) on a subject having a skin disorder, such as a *Molluscum contagiosum* infection.

As noted above, in some embodiments, the composition may have beneficial properties that contribute, at least in part, to the efficacy and/or safety of the methods described herein. In some embodiments, the composition may comprise a relatively low concentration of cantharidin and have a relatively low vapor pressure (e.g., less than or equal to about 210 mm Hg at 20° C., less than or equal to about 126 mm Hg at 20° C.). For instance, the composition may comprise a relatively low concentration of cantharidin (e.g., less than or equal to about 1.2% (w/v)), a non-aqueous solvent (e.g., ethanol and acetone), a film-forming agent (e.g., nitrocellulose and/or hydroxypropyl cellulose), and a plasticizer (e.g., camphor and/or castor oil). In some embodiments, the composition may also comprise a dye (e.g., gentian violet) and/or a bittering agent (e.g., denatonium benzoate).

In one example, the composition may comprise cantharidin (e.g., in an amount of greater than or equal to about 0.1 and less than or equal to about 1.2 weight per volume percent, in an amount of greater than or equal to about 0.7 and less than or equal to about 0.9 weight per volume percent, 0.7 weight per volume percent), acetone (e.g., in an amount of greater than or equal to about 55 and less than or equal to about 65 weight per weight percent, in an amount of to greater than or equal to about 58 and less than or equal to about 62 weight per weight percent), ethanol (e.g., in an amount of greater than or equal to about 25 and less than or equal to about 35 weight per weight percent, in an amount of greater than or equal to about 28 and less than or equal to about 32 weight per weight percent), castor oil (e.g., in an amount of greater than or equal to about 0.5 and less than or equal to about 2 weight per weight percent, in an amount of, greater than or equal to about 1.2 and less than or equal to about 1.6 weight per weight percent), nitrocellulose (e.g., in an amount of greater than or equal to about 2 and less than or equal to about 10 weight per weight percent, in an amount of greater than or equal to about 3 and less than or equal to about 6 weight per weight percent of nitrocellulose), hydroxypropyl cellulose (in an amount of greater than or equal to about 0.1 and less than or equal to about 2 weight per weight percent, in an amount of greater than or equal to about 0.1 and less than or equal to about 2 weight per weight percent), camphor (e.g., in an amount of greater than or equal to about 0.1 and less than or equal to about 2 weight per weight percent, in an amount of greater than or equal to about 0.5 and less than or equal to about 1.5 weight per weight percent), denatonium benzoate (e.g., in an amount of greater than or equal to about 0.001 and less than or equal to about 0.01 weight per weight percent, in an amount of greater than or equal to about 0.004 and less than or equal to about 0.008 weight per weight percent), and/or gentian violet (e.g., in an amount of greater than or equal to about 0.0001 and less than or equal to about 0.001 weight per weight percent of gentian violet, in an amount of greater than or equal to about 0.0002 and less than or equal to about 0.0008 weight per weight percent).

In some embodiments, the overall solvent and/or the composition may have a certain vapor pressure that imparts beneficial properties to the composition. For instance, the overall solvent in the composition and/or the composition may have a vapor pressure of less than or equal to about 210 mm Hg, less than or equal to about 200 mm Hg, less than or equal to about 175 mm Hg, less than or equal to about 150 mm Hg, or less than or equal to about 126 mm Hg at 20° C. In some embodiments, the vapor pressure of the overall solvent and/or the composition may be greater than or equal to about 100 mm Hg and less than or equal to about 210 mm Hg (e.g., greater than or equal to about 100 mm Hg and less than or equal to about 200 mm Hg, greater than or equal to about 100 mm Hg and less than or equal to about 175 mm Hg, greater than or equal to about 100 mm Hg and less than or equal to about 150 mm Hg) at 20° C. In certain embodiments, the overall solvent in the composition and/or the composition may have a flash point of greater than or equal to about 4° C. In some embodiments, the overall solvent in the composition and/or the composition may not form peroxide groups upon degradation or otherwise have the propensity to from peroxides.

In certain embodiments, one or more solvent components (e.g., all solvent components) in the overall solvent, the overall solvent and/or the composition may have a vapor pressure less than or equal to about 350 mm Hg, less than or equal to about 340 mm Hg, less than or equal to about 330 mm Hg, less than or equal to about 320 mm Hg, less than or equal to about 310 mm Hg, less than or equal to about 300 mm Hg, less than or equal to about 290 mm Hg, less than or equal to about 280 mm Hg, less than or equal to about 270 mm Hg, less than or equal to about 260 mm Hg, less than or equal to about 250 mm Hg, less than or equal to about 240 mm Hg, less than or equal to about 230 mm Hg, less than or equal to about 220 mm Hg, less than or equal to about 210 mm Hg, less than or equal to about 200 mm Hg, less than or equal to about 190 mm Hg, less than or equal to about 180 mm Hg, less than or equal to about 170 mm Hg, less than or equal to about 160 mm Hg, less than or equal to about 150 mm Hg, less than or equal to about 140 mm Hg, less than or equal to about 130 mm Hg, less than or equal to about 120 mm Hg, less than or equal to about 110 mm Hg, less than or equal to about 100 mm Hg, less than or equal to about 90 mm Hg, less than or equal to about 80 mm Hg, less than or equal to about 70 mm Hg, less than or equal to about 60 mm Hg, or less than or equal to about 50 mm Hg at 20° C. In some instances, one or more solvent components in the overall solvent, the overall solvent and/or the composition may have a vapor pressure greater than or equal to about 20 mm Hg, greater than or equal to about 25 mm Hg, greater than or equal to about 30 mm Hg, greater than or equal to about 35 mm Hg, greater than or equal to about 40 mm Hg, greater than or equal to about 50 mm Hg, greater than or equal to about 60 mm Hg, greater than or equal to about 70 mm Hg, greater than or equal to about 80 mm Hg, greater than or equal to about 90 mm Hg, greater than or equal to about 100 mm Hg, greater than or equal to about 110 mm Hg, or greater than or equal to about 120 mm Hg at 20° C. All combinations of the above-referenced ranges are possible. In some embodiments, one or more solvent components (e.g., all solvent components) in the overall solvent, the overall solvent and/or the composition may have a vapor pressure of less than or equal to about 210 mm Hg (e.g., less than or equal to about 200 mm Hg, 185 mm Hg) at 20° C. In certain embodiments, one or more solvent components (e.g., all solvent components) in the overall solvent may have a flash point of greater than or equal to about 4° C. In certain embodiments, the composition may not comprise a solvent components having a flash point of less than or equal to about 4° C. In other embodiments, the composition may comprise less than or equal to about 20 wt. % of solvent components having a flash point of less than or equal to about 4° C. In some embodiments, one or more solvent components (e.g., all solvent components) in the overall solvent may not form peroxide groups upon degradation or otherwise have the propensity to from peroxide groups.

In some embodiments, the composition may comprise a relatively low percentage of diethyl ether (e.g., less than or equal to about 20% w/w, less than or equal to about 15% w/w, less than or equal to about 10% w/w, less than or equal to about 5% w/w, less than or equal to about 1% w/w, less than or equal to about 0.1% w/w, less than or equal to about 0.01% w/w) or may not comprise diethyl ether. In some embodiments, the composition may comprise a relatively low percentage of water (e.g., less than or equal to about 10% w/w, less than or equal to about 5% w/w, less than or equal to about 1% w/w, less than or equal to about 0.1% w/w, less than or equal to about 0.01% w/w) or may not comprise water.

In some embodiments, the methods, described herein, may comprise administering the composition using a single-use applicator. In certain embodiments, the methods, described herein, may comprise administering the composition using a multi-use applicator. Suitable applicators are described in International Publication No. PCT/US2014/052184, filed Aug. 21, 2014 and entitled "Compositions, Methods, and Systems for the Treatment of Cutaneous Disorders," and U.S. Provisional Application, U.S. Ser. No.

62/520,0504, filed Jun. 15, 2017, and entitled "Devices and Methods for the Treatment of Cutaneous Disorders," which are incorporated by reference in their entirety. International Publication No. PCT/US2015/066487, filed Dec. 17, 2015 and entitled "Commercially Viable Synthesis of Cantharidin and Bioactive Cantharidin Derivatives," and International Publication No. PCT/US2016/014139, filed Jan. 20, 2016 and entitled "Quantification and Preparation of Pharmaceutical Grade Cantharidin," are also incorporated by reference in their entirety.

In some embodiments, the present disclosure provides a method for treating epithelial warts, *Molluscum contagiosum* or other skin diseases in a subject by using an applicator device comprising a reservoir and an applicator unit to administer the cantharidin formulation to the subject. The reservoir can contain a cantharidin formulation. The applicator unit can be in fluid communication with the reservoir. The cantharidin formulation can contain at least about 0.001% (w/v) cantharidin. In some cases, the cantharidin formulation can contain at least about 0.01%, 0.1%, 0.5%, 1.0%, 1.2%, or 1.5% cantharidin. The cantharidin formulation can contain greater than or equal to about 1% (w/v) of excipients. The epithelial lesions can be removed from the subject within two weeks after delivering the cantharidin formulation.

In some embodiments, the present disclosure provides a kit for administering a cantharidin formulation to a subject. The kit can comprise a plurality of separately packaged, individually removable, dosage units in liquid or gel form. In some examples, a dosage unit is in a delivery device or system. In some cases, a dosage unit is in a packaging unit (e.g., ampule).

In some situations, a dosage unit can contain the cantharidin formulation in an amount from about 0.1 mL to about 10 mL. The cantharidin formulation contains at least about 0.001% of cantharidin. In some cases, the cantharidin formulation can contain at least about 0.01%, 0.1% or 1% cantharidin. The kit can be used for administering each of the active dosage units. The dosage units comprising the cantharidin formulation can be therapeutically effective for treating epithelial warts or other lesions in the subject. The kit can comprise at least three packaging units. The dosage unit containing the cantharidin formulation can be therapeutically effective in reducing epithelial warts or other lesions by at least about 50% in volume over the period of about 7 days.

In some embodiments, the present disclosure provides instructions for the optimal treatment schedule. Different doses of cantharidin, the preparation of the skin, the frequency and quantity applied to the skin, how the skin is cared for after application and the amount of time cantharidin is left in contact with the skin have not been thoroughly tested by others and are not intuitively obvious to those skilled in the art as evidenced by the variability in peer-reviewed publications. The methods herein allow for the optimally effective treatment of warts, *molluscum*, and/or other cutaneous disorders with a cantharidin formulation.

In some embodiments, average treatment time per lesion for a subject may be relatively short. For instance, the average treatment time per lesion may be less than or equal to about 30 seconds, less than or equal to about 25 seconds, less than or equal to about 15 seconds, less than or equal to about 10 seconds, or less than or equal to about 5 seconds. The average treatment time may be determined by measuring the time period from the start of treatment of the first lesion to the conclusion of treatment of the last lesion for a given administration step and dividing the time period by the number of lesions treated. For example, the average treatment time for a subject having 10 lesions that are treated over a 50 second time period is 5 seconds.

In some situations, the cantharidin formulation can be administered, such that the average treatment time and/or time period is less than or equal to about 30 seconds. The cantharidin formulation can be administered, such that the average treatment time and/or time period is less than or equal to about 20 seconds. The cantharidin formulation can be administered, such that the average treatment time and/or time period is less than or equal to about 10 seconds. The cantharidin formulation can be administered, such that the average treatment time and/or a time period less than or equal to about 5 seconds.

In some situations, the cantharidin formulation can be administered at a volume that is less than or equal to about 10 µL of the cantharidin formulation. In other situations, the cantharidin formulation can be administered at a volume that is less than or equal to about 5 µL of the cantharidin formulation.

In some embodiments, the present disclosure provides a kit for administering a cantharidin formulation to a subject that comprises a plurality of separately packaged, individually removable, dosage units in liquid or gel form, wherein the dosage units can be in a packaging unit, wherein the dosage units each contains the cantharidin formulation in an amount from about 0.01 mL to 10 mL. The cantharidin formulation may contain at least about 0.001% (w/v) of cantharidin. In some cases, the cantharidin formulation can contain at least about 0.01%, 0.1%, or 1% cantharidin.

In some situations, the kit can further include instructional material for administering the cantharidin formulation. The instructional material for allowing at least a portion of the composition to remain on the skin lesion for a certain period of time (e.g., greater than about 6 hours). The instructional material can enable the subject to self-administer the cantharidin formulation. The instructional material may be for treating an epithelial wart in the subject. The kit may comprise at least three packaging units. The cantharidin formulation can be suitable for removing an epithelial wart from the subject within two weeks after delivering the dosage unit comprising the cantharidin formulation.

In some embodiments, the present disclosure provides a formulation that contains at least about 0.001% (w/v) of cantharidin, a flavorant that can induce a bitter taste in a subject upon ingestion of the formulation by the subject, and a colorant that can enable visible detection of the formulation by the subject. The formulation may have a volume of at most about 10 milliliters (mL).

In some situations, the cantharidin formulation may contain at least about 0.001% cantharidin. The cantharidin formulation may contain at least about 0.01%, 0.1%, 0.5% or 1% cantharidin. The flavorant and/or colorant can be at a concentration of at most about 1% (w/v). The volume can be less than or equal to about 5 mL. The formulation can have a Reynolds number less than about 1500 at 25° C. The formulation may further comprise a gelling agent. The formulation can have a manganese or magnesium ion concentration that is less than about 1%. The flavorant can be selected from the group consisting of denatonium, amarogentin, gentiopicrin, sucrose octaacetate, quercetin, brucine and quassin. The colorant can be selected from the group consisting of D&C violet, isosulfan blue, methylene blue, methyl red, methyl orange, congo red, alizarin yellow, bromocresol green, FD&C Green 3, FD&C Yellow 5, and gentian violet.

In some embodiments, the present disclosure provides a method for treating a skin ailment (e.g., wart) on a skin (or skin location) of a subject, comprising a) providing a cantharidin formulation that comprises (i) at least about 0.001% (w/v) of cantharidin, (ii) a flavorant that can induce a bitter taste in a subject upon ingestion of the formulation by the subject, and a colorant that can enable visible detection of the formulation by the subject, and b) providing the cantharidin formulation to the skin at a location that contains or is suspected of containing the skin ailment. The formulation can have a volume of at most about 10 milliliters (mL)

In some situations, the cantharidin formulation may contain at least about 0.001% cantharidin. The cantharidin formulation may contain at least about 0.01%, 0.1%, 0.5%, or 1% cantharidin. The flavorant and/or colorant can be at a concentration of at most about 1% (w/v). The volume can be less than or equal to about 5 mL. The formulation can have a Reynolds number less than about 1500 at 25° C. The method may further comprise a gelling agent. The formulation can have a manganese or magnesium ion concentration that is less than about 1%. The flavorant can be selected from the group consisting of denatonium, amarogentin, gentiopicrin, sucrose octaacetate, quercetin, brucine and quassin. The colorant can be selected from the group consisting of D&C violet, isosulfan blue, methylene blue, methyl red, methyl orange, congo red, alizarin yellow, bromocresol green, and gentian violet. The skin ailment can be selected from the group consisting of wart, *Molluscum contagiosum*, seborrheic keratosis, and actinic keratosis.

therapeutic benefit and/or a prophylactic benefit. By therapeutic benefit is meant eradication or amelioration of the underlying disorder being treated, such as a skin disease or ailment, such as warts. Also, a therapeutic benefit can be achieved with the eradication or amelioration of one or more of the physiological symptoms associated with the underlying disorder, such that an improvement is observed in the patient, notwithstanding that the patient may still be afflicted with the underlying disorder. Treatment can include diagnosis of a health condition, such as warts.

The term "cantharidin," as used herein, generally refers to a compound of the structure below, or a derivative thereof that has similar activity with regard to protein phosphatase inhibition. Compounds in which boron has been substituted in place of carbon may also be considered cantharidin. Compounds with differing proportions of carbon isotopes may also be considered cantharidin (e.g., $C^{14}$). Compounds with differing proportions of oxygen isotopes may also be considered cantharidin (e.g., $O^{17}$). Compounds with different proportions of hydrogen isotopes may also be considered cantharidin ($H^3$). Compounds with different proportions of carbon, oxygen, hydrogen isotopes or combinations thereof may also be considered cantharidin. Cantharidin may comprise one or more unstable radioactive elements. Cantharidin may not comprise one or more unstable radioactive elements. Cantharidin may comprise a pharmaceutically acceptable salt. Cantharidin may not comprise a pharmaceutically acceptable salt.

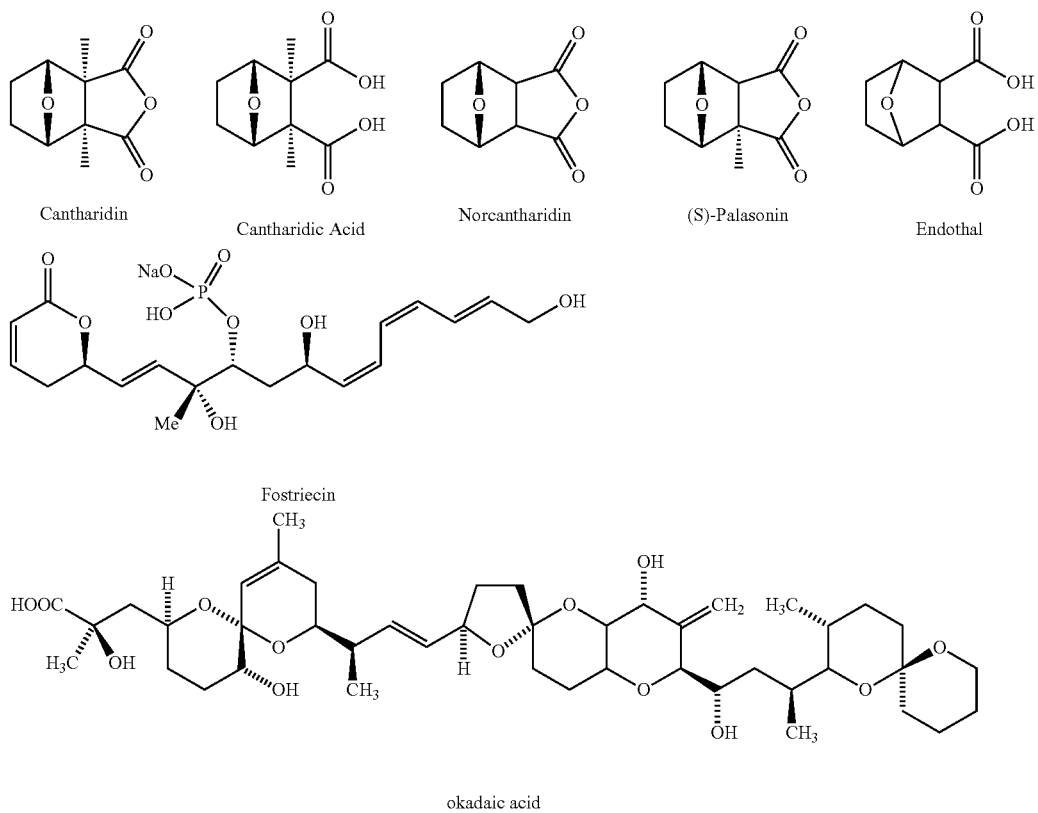

The term "treatment" or "treating," as used herein, generally refers to an approach for obtaining beneficial, predetermined or desired results, including, but not limited to, Non-limiting examples of cantharidin derivatives include cantharidic acid, norcantharidin, palasonin, endothal, fostriecin and okadaic acid (see above). Other species with or without substitutions that have an exo,exo-dicarbolic acid or which may be expected to breakdown or be metabolized into the species containing an exo,exo-dicarbolic acid may also be considered "cantharidin". Other compounds that serve as inhibitors of protein phosphatases 1, 2A, 4 or 5 may also be considered "cantharidin." A cantharidin formulation can comprise cantharidin alone or in addition to one or more other species, such as one or more excipients.

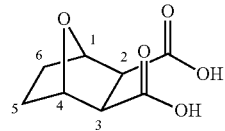

Non limiting examples of substituted exo,exo-dicarbolic acids include: 2,3-trimethylene anhydride; unsubstituted-anhydride; 5,6-dehydro-anhydride; endo-5-methyl; mono-4-chloranilide; endo-5-carboxy; 5,6-dehydro; 2-bromo; endo-5-hydroxymethyl.

Cantharidin may be produced by one or more blister beetles including but not limited to Spanish fly beetles, false blister beetles, cardinal beetles, soldier beetles, Chinese blister beetles or combinations thereof. The amount of cantharidin produced per blister beetle may be about 0.1, 0.2, 0.3, 0.4, 0.5, 0.6, 0.7, 0.8, 0.9, 1, 1.5, 2, 2.5, 3, 3.5, 4, 4.5, 5, 5.5, or about 6 mg. The amount of cantharidin produced per blister beetle may be more than about 0.1, 0.2, 0.3, 0.4, 0.5, 0.6, 0.7, 0.8, 0.9, 1, 1.5, 2, 2.5, 3, 3.5, 4, 4.5, 5, 5.5, 6 mg or more. The amount of cantharidin produced per blister beetle may be less than about 0.1, 0.2, 0.3, 0.4, 0.5, 0.6, 0.7, 0.8, 0.9, 1, 1.5, 2, 2.5, 3, 3.5, 4, 4.5, 5, 5.5, 6 mg or less. Cantharidin may be produced by biosynthesis. In some cases, biosynthesis of derivatives of cantharidin, norcantharidin, cantharidimide, or norcantharimide produces similar therapeutic effects in the user or patient. As an alternative, cantharidin can be produced fully synthetically or semi-synthetically, for example, using naturally occurring raw materials.

The term "excipient," as used herein, generally refers to an inactive ingredient as part of a formulation. Examples of excipients include, without limitations, dyes, flavors, binders, emollients, fillers, lubricants, antioxidants, skin penetration enhancers and preservatives. In some cases, an excipient can be selected from lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup and methyl cellulose. In some embodiments, an excipient can be salicylic acid and/or podophyllotoxin.

The term "user," as used herein, generally refers to an individual using a delivery device or system to administer a cantharidin formulation to her or himself, or another individual, such as a subject.

The term "subject," as used herein, generally refers to an individual that is suspected of having an ailment (e.g., skin ailment), that has been diagnosed with the ailment, or is under treatment. For example, a subject can be under treatment by another individual or being administered a cantharidin formulation of the disclosure, either by him or herself or by another individual, such as a healthcare provider (e.g., physician, treating physician, physician's assistant, nurse) or a care provider. A subject can include asymptomatic individuals and symptomatic individuals, such as a patient. In some cases, the subject can be diagnosed with a skin disease.

The term "about" as used herein refers to within plus or minus (+/−) 10%, 9%, 8%, 7%, 6%, 5%, 4%, 3%, 2%, or 1% of the designated amount.

In some embodiments, the present disclosure provides cantharidin formulations for treating skin conditions, ailments and/or diseases, such as cutaneous warts. A cantharidin formulation can include a therapeutically effective amount of cantharidin.

In general, the composition comprising cantharidin is administered topically. For example, the composition may be administered to a particular location on the subject, such as the skin, without systemic administration. In some such cases, a composition, which is topically administered, may be therapeutically effective at or around the location to which the composition is administered, but may not be therapeutically effective elsewhere. In certain embodiments, the composition is administered topically to the skin, such that relatively little (e.g., plasma concentration of less than or equal to about 3.3 ng/mL, plasma concentration of less than or equal to about 2.5 ng/mL, plasma concentration of less than or equal to about 1 ng/mL) or no cantharidin is present systemically after topical administration. In some cases, a cantharidin formulation for topical delivery comprises cantharidin and excipients suitable for topical delivery of cantharidin to a subject. The amount of cantharidin in the cantharidin formulation is not particularly limited. The amount of a formulation may be limited to a therapeutic amount. In some circumstances, it may be advantageous to include amounts of cantharidin far in excess of nominal therapeutic amounts, for example to maximize the concentration of cantharidin. In other embodiments, it may be advantageous to limit the amounts of cantharidin based on toxicity to the subject.

In some cases, a cantharidin formulation can comprise at least about 50% (w/v) of cantharidin, at least about 10% (w/v) of cantharidin, at least about 5% (w/v) of cantharidin, at least about 1% (w/v) of cantharidin, at least about 0.75% (w/v) of cantharidin, at least about 0.5% (w/v) of cantharidin, at least about 0.1% (w/v) of cantharidin, at least about 0.01% (w/v) of cantharidin, or at least about 0.001% (w/v) of cantharidin. Cantharidin may be present in an amount between about 0.001% and 50% by weight, or between about 1% and about 10% by weight, or between about 0.001% and 1% by weight. Cantharidin may be present in an amount of about 0.001, 0.01, 0.1, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, or about 15 grams per ml. Cantharidin may be present in an amount of more than about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15 grams or more per ml. Cantharidin may be present in an amount of less than about 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15 grams or less per ml.

A cantharidin formulation can have a cantharidin concentration (milligram (mg) cantharidin/milliliter (mL) formulation) of about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL, 6.0 mg/mL, 6.1 mg/mL, 6.2 mg/mL, 6.3 mg/mL, 6.4 mg/mL, 6.5 mg/mL, 6.6 mg/mL, 6.7 mg/mL, 6.8 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, 8.9 mg/mL, 9.0 mg/mL, 9.1 mg/mL, 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL, 10.1 mg/mL, 10.2 mg/mL, 10.3 mg/mL, 10.4 mg/mL, 10.5 mg/mL, 10.6 mg/mL, 10.7 mg/mL, 10.8 mg/mL, 10.9 mg/mL, 11.0 mg/mL, 11.1 mg/mL, 11.2 mg/mL, 11.3 mg/mL, 11.4 mg/mL, 11.5 mg/mL, 11.6 mg/mL, 11.7 mg/mL, 11.8 mg/mL, 11.9 mg/mL, 12.0 mg/mL, 12.1 mg/mL, 12.2 mg/mL, 12.3 mg/mL, 12.4 mg/mL, 12.5 mg/mL, 12.6 mg/mL, 12.7 mg/mL, 12.8 mg/mL, 12.9 mg/mL, 13.0 mg/mL, 13.1 mg/mL, 13.2 mg/mL, 13.3 mg/mL, 13.4 mg/mL, 13.5 mg/mL, 13.6 mg/mL, 13.7 mg/mL, 13.8 mg/mL, 13.9 mg/mL, 14.0 mg/mL, 14.1 mg/mL, 14.2 mg/mL, 14.3 mg/mL, 14.4 mg/mL, 14.5 mg/mL, 14.6 mg/mL, 14.7 mg/mL, 14.8 mg/mL, 14.9 mg/mL, 15.0 mg/mL, 15.5 mg/mL, 16.0 mg/mL, 16.5 mg/mL, 17.0 mg/mL, 17.5 mg/mL, 18.0 mg/mL, 18.5 mg/mL, 19.0 mg/mL, 19.5 mg/mL, or 20.0 mg/mL. In some examples, the cantharidin concentration is an amount of 0.5 milligrams (mg) to 20 mg per milliliter (ml), or 1 mg to 10 mg per ml.

As an alternative, a cantharidin formulation can have a cantharidin concentration (mg cantharidin/mL formulation) of at least about 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 1.1 mg/mL, 1.2 mg/mL, 1.3 mg/mL, 1.4 mg/mL, 1.5 mg/mL, 1.6 mg/mL, 1.7 mg/mL, 1.8 mg/mL, 1.9 mg/mL, 2.0 mg/mL, 2.1 mg/mL, 2.2 mg/mL, 2.3 mg/mL, 2.4 mg/mL, 2.5 mg/mL, 2.6 mg/mL, 2.7 mg/mL, 2.8 mg/mL, 2.9 mg/mL, 3.0 mg/mL, 3.1 mg/mL, 3.2 mg/mL, 3.3 mg/mL, 3.4 mg/mL, 3.5 mg/mL, 3.6 mg/mL, 3.7 mg/mL, 3.8 mg/mL, 3.9 mg/mL, 4.0 mg/mL, 4.1 mg/mL, 4.2 mg/mL, 4.3 mg/mL, 4.4 mg/mL, 4.5 mg/mL, 4.6 mg/mL, 4.7 mg/mL, 4.8 mg/mL, 4.9 mg/mL, 5.0 mg/mL, 5.1 mg/mL, 5.2 mg/mL, 5.3 mg/mL, 5.4 mg/mL, 5.5 mg/mL, 5.6 mg/mL, 5.7 mg/mL, 5.8 mg/mL, 5.9 mg/mL, 6.0 mg/mL, 6.1 mg/mL, 6.2 mg/mL, 6.3 mg/mL, 6.4 mg/mL, 6.5 mg/mL, 6.6 mg/mL, 6.7 mg/mL, 6.8 mg/mL, 6.9 mg/mL, 7.0 mg/mL, 7.1 mg/mL, 7.2 mg/mL, 7.3 mg/mL, 7.4 mg/mL, 7.5 mg/mL, 7.6 mg/mL, 7.7 mg/mL, 7.8 mg/mL, 7.9 mg/mL, 8.0 mg/mL, 8.1 mg/mL, 8.2 mg/mL, 8.3 mg/mL, 8.4 mg/mL, 8.5 mg/mL, 8.6 mg/mL, 8.7 mg/mL, 8.8 mg/mL, 8.9 mg/mL, 9.0 mg/mL, 9.1 mg/mL, 9.2 mg/mL, 9.3 mg/mL, 9.4 mg/mL, 9.5 mg/mL, 9.6 mg/mL, 9.7 mg/mL, 9.8 mg/mL, 9.9 mg/mL, 10.0 mg/mL, 10.1 mg/mL, 10.2 mg/mL, 10.3 mg/mL, 10.4 mg/mL, 10.5 mg/mL, 10.6 mg/mL, 10.7 mg/mL, 10.8 mg/mL, 10.9 mg/mL, 11.0 mg/mL, 11.1 mg/mL, 11.2 mg/mL, 11.3 mg/mL, 11.4 mg/mL, 11.5 mg/mL, 11.6 mg/mL, 11.7 mg/mL, 11.8 mg/mL, 11.9 mg/mL, 12.0 mg/mL, 12.1 mg/mL, 12.2 mg/mL, 12.3 mg/mL, 12.4 mg/mL, 12.5 mg/mL, 12.6 mg/mL, 12.7 mg/mL, 12.8 mg/mL, 12.9 mg/mL, 13.0 mg/mL, 13.1 mg/mL, 13.2 mg/mL, 13.3 mg/mL, 13.4 mg/mL, 13.5 mg/mL, 13.6 mg/mL, 13.7 mg/mL, 13.8 mg/mL, 13.9 mg/mL, 14.0 mg/mL, 14.1 mg/mL, 14.2 mg/mL, 14.3 mg/mL, 14.4 mg/mL, 14.5 mg/mL, 14.6 mg/mL, 14.7 mg/mL, 14.8 mg/mL, 14.9 mg/mL, 15.0 mg/mL, 15.5 mg/mL, 16.0 mg/mL, 16.5 mg/mL, 17.0 mg/mL, 17.5 mg/mL, 18.0 mg/mL, 18.5 mg/mL, 19.0 mg/mL, 19.5 mg/mL, or 20.0 mg/mL. In some situations, the cantharidin formulation can have a cantharidin concentration that is less than or equal to about 40 mg/mL, 30 mg/mL, 20 mg/mL, 10 mg/mL, 5 mg/mL, or 1 mg/mL.

The cantharidin used in the formulation may be of sufficient purity to induce a therapeutic effect without associated toxicity. Purity of the cantharidin used in the formulation may be between 50% and 100%. The purity of the cantharidin used may be greater than or equal to about 70%, 80%, 90%, 95%, 98%, 99%, or 99.9%.

In some embodiments, cantharidin can be formulated into preparations in solid, semi-solid, gel, or liquid forms suitable for local or topical administration, such as gels, water-soluble jellies, creams, lotions, suspensions, solutions, foams, powders, slurries, ointments, solutions, oils, capsules, tablets, pastes, suppositories, sprays, emulsions, saline solutions, dimethylsulfoxide (DMSO)-based solutions, suitable for local or topical administration. Carriers with high densities may be capable of providing an area with a prolonged exposure to the active ingredients. In contrast, a solvent/solution formulation may provide more immediate exposure of cantharidin to the chosen area.

A cantharidin formulation may also comprise suitable solid, semi-solid, gel or liquid phase carriers or excipients, which are compounds that may provide increased penetration of, or modify the delivery of, therapeutic molecules across the stratum corneum permeability barrier of the skin. Examples of such carriers and excipients include, but are not limited to, destructive agents (e.g., bases, acids, oxidizers), crosslinking agents (e.g. formalin or formaldehyde), humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

A cantharidin formulation can contain an acid or combination of acids, including, but not limited to, salicylic acid, trichloroacetic acid, hydrochloric acid, formic acid, squaric acid or nitric acid. A cantharidin formulation can contain podophyllotoxin. A cantharidin formulation can contain zinc oxide. A cantharidin formulation can contain immunotheraputics such as imiquimod, 2,4-Dinitrochlorobenzene and/or *candida* antigen. A cantharidin formulation can contain chemotherapeutics such as bleomyocin, podophyllotoxin and/or fluorouracil. A cantharidin formulation can contain an oxidizer, such as hydrogen peroxide.

A cantharidin formulation can include a solubilizer to ensure good solubilization and/or dissolution of cantharidin and to minimize precipitation of cantharidin in the formulation. A solubilizer may be added to increase the solubility of cantharidin and/or to maintain the composition as a stable or homogeneous solution, emulsion or dispersion.

Examples of suitable solubilizers include, but are not limited to, one or more of the following: alcohols and polyols, such as acetone, ethanol, isopropanol, butanol, benzyl alcohol, ethylene glycol, propylene glycol, butane-diols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose, hydroxyethylcellulose, hyroxypropylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, ε-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, ε-caprolactone and isomers thereof, δ-valerolactone and isomers thereof, β-butyrolactone and isomers thereof; and other solubilizers, such as dimethyl acetamide, dimethyl isosorbide, N-methyl pyrrolidones, monooctanoin, diethylene glycol monoethyl ether, and water.

Mixtures of solubilizers may also be used. Examples include, but are not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, polyethylene glycol 200-100, glycofurol, transcutol, propylene glycol, dimethyl isosorbide, sorbitol, glycerol, triacetin, ethyl alcohol, PEG-400, glycofurol and propylene glycol.

The amount of a given solubilizer may be limited to a bio-acceptable amount. In some circumstances, it may be advantageous to include amounts of solubilizers in excess of bioacceptable amounts, for example to maximize the concentration of the drug, with excess solubilizer removed prior to providing the composition to a subject using conventional techniques, such as distillation or evaporation. A solubilizer, if present, can be in a weight ratio of 10%, 25%, 50%, 100%, or up to about 200% by weight, based on the combined weight of cantharidin, and other excipients. As an alternative, substantially low amounts of solubilizer may also be used, such as 5%, 2%, 1% or even less by weight of the cantharidin formulation. In some examples, the solubilizer may be present in an amount of about 1% to about 100%, or about 5% to about 25% by weight of the cantharidin formulation. In some cases, a cantharidin formulation includes less than a bio-acceptable amount.

A cantharidin formulation can comprise one or more film-forming agents. A cantharidin formulation may not comprise one or more film-forming agents. Some examples of film-forming agent may include but are not limited to nitrocellulose, nitrocellulose derivatives, polyvinyl pyrrolidone, hydroxypropylmethycellulose, carboxymethylcellulose and other film-forming agents or combinations thereof. The film-forming agent may be dissolved in a solvent. The film-forming agent may be dissolved in one or more solvents. A cantharidin formulation may include one or more solvents. The solvents comprise ethanol, acetone, methanol, isopropyl alcohol, butyl alcohol, pentanol, ether, water, dimethyl sulfoxide, ethyl lactate, ethyl acetate, butyl acetate, isoprorpanol, acetonitrile, food grade oils (e.g., olive oil, canola oil, sunflower oil), chlorobutanol in a waxy base, bee's wax, lanolin, petroleum jelly, silicon oil, or combinations thereof, or other solvents. In some embodiments, the solvent is a pharmaceutically acceptable solvent. In some cases, the solvent is not or does not include diethyl ether. The solvent may be acetone. In some embodiments, the solvent comprises acetone and an alcohol (e.g., ethanol). A cantharidin formulation may comprise one or more plasticizers. A cantharidin formulation may not comprise one or more plasticizers. Examples of such plasticizers may include but are not limited to camphor and castor oil. A cantharidin formulation can comprise one or more water-mediated polymerization agents. A cantharidin formulation may not comprise one or more water-mediated polymerization agents. Examples of water-mediated polymerization agents may include, but are not limited to, 2-octyl cyanoacrylate and butyl cyanoacrylate. In some cases, including a film-forming agent, a plasticizer, a water-mediated polymerization agent or combinations thereof, provides a final cantharidin formulation with viscosity, flexibility, durability, rigidity, ruggedness and or film-forming properties.

In some cases, one or more film-forming agents are present in a cantharidin formulation at a weight-to-volume concentration of between about 0.1% to about 10%. In some cases, one or more film-forming agents is present in a cantharidin formulation at a weight-to-volume concentration of about 1.25%. In some cases, one or more film-forming agents are present in a cantharidin formulation at a weight-to-volume concentration of about 2%. In some cases, one or more film-forming agents is present in a cantharidin formulation at a weight-to-volume concentration of about 0.001, 0.01, 0.1, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, or 25%. In some cases, one or more film-forming agents is present in a cantharidin formulation at a weight-to-volume concentration of more than about 0.001, 0.01, 0.1, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25%, or more. In some cases, one or more film-forming agents is present in a cantharidin formulation at a weight-to-volume concentration of less than about 0.001, 0.01, 0.1, 1, 1.25, 1.5, 1.75, 2, 2.25, 2.5, 2.75, 3, 3.25, 3.5, 3.75, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 15.5, 16, 16.5, 17, 17.5, 18, 18.5, 19, 19.5, 20, 21, 22, 23, 24, 25%, or less.

In some cases, the one or more solvents is present in a cantharidin formulation at a weight-to-volume concentration of between about 10% to about 95%. In some cases, the one or more solvents is present in a cantharidin formulation at a weight-to-volume concentration of about 13%. In some cases, the one or more solvents is present in a cantharidin formulation at a weight-to-volume concentration of about 87%. In some cases, the one or more solvents is present in a cantharidin formulation at a weight-to-volume concentration of about 10, 15, 20, 25, 30, 35, 40, 45, 50, 55, 60, 65, 70, 75, 80, 85, 90, or 95%. In some cases, the one or more solvents is present in a cantharidin formulation at a weight-to-volume concentration of more than about 10, 15, 20, 25, 30, 35, 40, 45, 50, 55, 60, 65, 70, 75, 80, 85, 90, 95% or more. In some cases, the one or more solvents is present in a cantharidin formulation at a weight-to-volume concentration of less than about 10, 15, 20, 25, 30, 35, 40, 45, 50, 55, 60, 65, 70, 75, 80, 85, 90, 95% or less.

When applied to the skin, a cantharidin solution can dry rapidly, such as, e.g., within 1 second, 10 seconds, 30 seconds, 1 minute, 5 minutes or 10 minutes. In an example, an assay used to evaluate the drying time of a cantharidin formulation is to apply 4 microliters of cantharidin formulation evenly over a 3 mm diameter circle of skin with a pipette. In an example, the cantharidin formulation dries in less than 2 minutes or 30 seconds.

In some cases, the one or more plasticizers are present in a cantharidin formulation at a weight-to-volume concentration of between about 0.001% to about 5%. In some cases, a plasticizer is not present in a cantharidin formulation. In some cases, the one or more plasticizers is present in a cantharidin formulation at a weight-to-volume concentration of about 5% or less. In some cases, a plasticizer is present in a cantharidin formulation at a weight-to-volume concentration of about 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, or 5%. In some cases, a plasticizer is present in a cantharidin formulation at a weight-to-volume concentration of more than about 0.001, 0.01 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5% or more. In some cases, a plasticizer is present in a cantharidin formulation at a weight-to-volume concentration of less than about 0.001, 0.01, 0.1, 0.15, 0.2, 0.25, 0.3, 0.35, 0.4, 0.45, 0.5, 0.55, 0.6, 0.65, 0.7, 0.75, 0.8, 0.85, 0.9, 0.95, 1, 1.5, 2, 2.5, 3, 3.5, 4, 4.5, 5% or less.

A cantharidin formulation can comprise a dye. A cantharidin formulation may comprise one or more dyes. A cantharidin formulation may not comprise a dye. A dye may be an acridine, anthraquinone, arylmethane, azo, diazonium, nitro, phtalocyanine, quinone imine, tetrazolium, thiazole, xanthene, acid, basic, direct, mordant, natural or solvent dye used at a concentration sufficient to adjust the color of the cantharidin formulation.

A dye may be acridine orange, acriflavine, anthracene blue SWR, alizarin, alizarin red S (mordant red 3), nuclear fast red, auramine O, chromoxane cyanin R, pararosanilin, rosanilin, magenta II, new fuchsin, methyl violet 2B, methyl violet 6B, crystal violet, Hoffman's violet, methyl green, ethyl green, acid fuchsin (acid violet 19), fast red B, fast blue B, diazonium chloride, diazonium acid sulphate, diazonium alkyl sulphate, diazonium chloride, diazonium fluborates, or diazonium benzenesulphonates, picric acid, alcian blue, luxol fast blue, toluidine blue O, thionin, azure A, azure B, azure C, neutral red, safranin O, gallocyanin, gallamin blue, iodonitrotetrazolium, nitro blue tetrazolium, thioflavine T, pyronin Y, pyronin B, rhodamine B, martius yellow (acid yellow 24), eosin Y (acid red 87), biebrich scarlet (acid red 66), suphonated pararosanilin (basic red 9), pararosanilin (basic red 9), methylene blue (basic blue 9), congo red (direct red 28), erie garnet (direct red 10), sirius red F3B (direct red 80), hematein (natural black 1), chromoxane cyanine R (mordant blue 3), celestine blue B (mordant blue 14), kermes (natural red 3), carmine (natural red 3), lac (natural red 25), hematein (natural black 1), saffron (natural yellow 6), sudan III (solvent red 23), sudan IV (solvent red 24), oil red 0 (solvent red 27), sudan black B (solvent black 3), or others.

A dye can include a phase change dye. A dye may include more than one phase change dye. A dye may not include a phase change dye. Some examples of phase changes dyes may include but are not limited to D&C orange, neozapon red 492, orasol red G, direct brilliant pink B, direct red 3BL, supranol brilliant red 3BW, lemon yellow 6G, light fast yellow 3G, aizen spilon yellow C-GNH, bemachrome yellow GD sub, cartasol brilliant yellow 4GF, cibanone yellow 2G, orasol black RLI, orasol black CN, savinyl black RLSN, pyrazol black BG, morfast black 101, diaazol black RN, thermoplast blue 670, orasol blue GN, savinyl blue GLS, luxol fast blue MBSN, sevron blue SGMF, basacid blue 750, keyplast blue, neozapon black X51, classic solvent black 7, sudan blue 670, sudan yellow 146, sudan red 462, neptune red base NB543, neopen blue FF-4012, fatsol black BR, morton morplas magenta 36, or others.

A dye can include serve as an indicator dye. A dye may include more than one indicator dye. A dye may not include an indicator dye. Some examples of indicator dyes may include but are not limited to D&C violet, isosulfan blue, methylene blue, methyl red, methyl orange, congo red, alizarin yellow, bromocresol green, gentian violet, or others. A dye can include one or more phase change dyes and one or more indicator dyes or combinations thereof. Indicator dye(s) can be used at a concentration sufficient to demark the area treated with a cantharidin formulation.

A cantharidin formulation can contain a fluorophore. A cantharidin formulation may contain more than one fluorophore. A cantharidin formulation may not contain a fluorophore. A fluorophore may indicate the presence of a mineral (e.g., magnesium, calcium, zinc, copper, iron, lead, cadium, mercury, nickel, cobalt, aluminum, or lanthanides). A fluorophore may indicate the presence of magnesium. A fluorophore may indicate the presence of intracellular magnesium. A cantharidin formulation may contain a fluorophore that fluoresces under an ultra violet light. Examples of fluorescent indicators that fluoresce under ultra violet light may include but are not limited to mag-indo-1 or mag-fura-2. A cantharidin formulation may contain a fluorophore that fluoresces under visible light. Examples of fluorescent indicators that fluoresce under visible light may include but are not limited to magnesium green or mag-fluo-4.

A cantharidin formulation can comprise one or more fluorophores, one or more dyes, or combinations thereof. In some cases, the one or more fluorophores or one or more dyes is present in a cantharidin formulation in a weight-to-volume concentration of about 0.00001, 0.00005, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8 0.9, 1, or 10%. In some cases, the one or more fluorophores or one or more dyes is present in a cantharidin formulation in a weight-to-volume concentration of more than about 0.00001, 0.00005, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8 0.9, 1, 10% or more. In some cases, the one or more fluorophores or one or more dyes is present in a cantharidin formulation in a weight-to-volume concentration of less than about 0.00001, 0.00005, 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8 0.9, 1, 10% or less. In some cases, the one or more fluorophores or one or more dyes is present in a cantharidin formulation in a weight-to-volume concentration of between about 0.00001% and about 1%. In some cases, the one or more fluorophores or one or more dyes is present in a cantharidin formulation in a weight-to-volume concentration of about 0.005%.

A cantharidin formulation can contain one or more aversive agents such as bittering agents or oral deterrents. A bittering agent is an example of a flavorant. A bittering agent or oral deterrent can be used to prevent or deter oral ingestion of the formulation. A bittering agent or oral deterrent can be used to prevent or deter licking and/or ingestion of the formulation prior to, during or after it has been applied to the skin. Bittering agents or oral deterrents can include, but are not limited to, denatonium (e.g., denatonium benzoate, denatonium saccharide), amarogentin, gentiopicrin, sucrose octaacetate, quercetin, brucine, and quassin. Bittering agent, denatonium benzoate may be added to a cantharidin formulation.

An aversive agent may be present in a cantharidin formulation in a concentration of about 0.01, 0.02, 0.03, 0.04, 0.05, 0.06, 0.07, 0.08, 0.09, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or about 20 parts per million (ppm). In some cases, an aversive agent is present in a cantharidin formulation in a concentration of more than about 0.01, 0.02, 0.03, 0.04, 0.05, 0.06, 0.07, 0.08, 0.09, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 ppm or more. In some cases, an aversive agent is present in a cantharidin formulation in a concentration of less than about 0.01, 0.02, 0.03, 0.04, 0.05, 0.06, 0.07, 0.08, 0.09, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, 20 ppm or less. In some cases, an aversive agent is present in a cantharidin formulation in a concentration of between about 0.01 ppm to about 20 ppm.

In some cases, an aversive agent is present in a cantharidin formulation in a weight-to-volume concentration of about 0.00001% to about 1% of the total liquid volume. In some cases, an aversive agent is present in a cantharidin formulation in a weight-to-volume concentration of about 0.000001%, 0.00001%, 0.0001%, 0.001%, 0.01%, 0.1%, 1%, or about 2%. In some cases, an aversive agent is present in a cantharidin formulation in a weight-to-volume concentration of more than about 0.000001%, 0.00001%, 0.0001%, 0.001%, 0.01%, 0.1%, 1%, 2%, or more. In some cases, an aversive agent is present in a cantharidin formulation in a weight-to-volume concentration of less than about 0.000001%, 0.00001%, 0.0001%, 0.001%, 0.01%, 0.1%, 1%, 2%, or less. An aversive agent may be present in a cantharidin formulation in a weight-to-volume concentration of about 0.0006%. An aversive agent may be present in a cantharidin formulation in a weight-to-volume concentration of about 0.0001% to about 0.001%.

A cantharidin formulation can include one or more pharmaceutically acceptable additives or excipients. Such additives or excipients can include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In some cases, a cantharidin formulation can have a pH of about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, or about 12.0. As an alternative, a cantharidin formulation can have a pH of at least about 3.0, about 3.1, about 3.2, about 3.3, about 3.4, about 3.5, about 3.6, about 3.7, about 3.8, about 3.9, about 4.0, about 4.1, about 4.2, about 4.3, about 4.4, about 4.5, about 4.6, about 4.7, about 4.8, about 4.9, about 5.0, about 5.1, about 5.2, about 5.3, about 5.4, about 5.5, about 5.6, about 5.7, about 5.8, about 5.9, about 6.0, about 6.1, about 6.2, about 6.3, about 6.4, about 6.5, about 6.6, about 6.7, about 6.8, about 6.9, about 7.0, about 7.1, about 7.2, about 7.3, about 7.4, about 7.5, about 7.6, about 7.7, about 7.8, about 7.9, about 8.0, about 8.1, about 8.2, about 8.3, about 8.4, about 8.5, about 8.6, about 8.7, about 8.8, about 8.9, about 9.0, about 9.1, about 9.2, about 9.3, about 9.4, about 9.5, about 9.6, about 9.7, about 9.8, about 9.9, about 10.0, about 10.1, about 10.2, about 10.3, about 10.4, about 10.5, about 10.6, about 10.7, about 10.8, about 10.9, about 11.0, about 11.1, about 11.2, about 11.3, about 11.4, about 11.5, about 11.6, about 11.7, about 11.8, about 11.9, or about 12.0.

A cantharidin formulation may be in liquid form. The liquid form may have a resistance to fluid flow. The liquid form may have a Reynolds number less than about 4000, 3000, 2000, 1500, 1000, 500, 400, 300, 200, or 100. The liquid form may have a Reynolds number that is about 0.1, 1, 5, 10, 25, 50, 75, 100, 250, 500, 1000, 1250, 1500, 1750, or about 2000. The liquid form may have a Reynolds number that is less than about 2000, 1750, 1500, 1250, 1000, 500, 400, 300, 250, 200, 150, 100, 75, 50, 25, 10, 5, 1, 0.1, or less.

In some cases, a cantharidin formulation may have a Reynolds number less than about 4000, 3000, 2000, 1500, 1000, 500, 400, 300, 200, or 100 at a temperature of about 25° C. The liquid form may have a Reynolds number that is about 1, 5, 10, 25, 50, 75, 100, 250, 500, 1000, 1250, 1500, 1750, or about 2000 at a temperature of about 25° C. The liquid form may have a Reynolds number that is less than about 2000, 1750, 1500, 1250, 1000, 500, 400, 300, 250, 200, 150, 100, 75, 50, 25, 10, 5, 1, or less at a temperature of about 25° C.

The liquid form may have a high viscosity. The liquid form may be substantially viscous such that the liquid may not splash, drip, run, drain, leak, aerosolize out of the applicator unit. The liquid form may be substantially viscous such that the cantharidin formulation remains at the location on the patient or on the user where it was administered. The liquid form may be substantially viscous such that the cantharidin formulation may not flow, splash, drip, run, drain, or leak from the location on the patient or on the user where it was administered.

One or more gelling agents may be added to the liquid form to increase viscosity, for example, dextran, nitrocellulose, hydroxypropyl cellulose, ethyl cellulose, or others. The viscosity of the liquid form at ambient conditions (e.g., 25° C.) may be about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, or about 2,000,000 centipoise. The viscosity of the liquid form at ambient conditions may be more than about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, 2,000,000 centipoise or more. The viscosity of the liquid form at ambient conditions may be less than about 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 90,000, 100,000, 110,000, 120,000, 130,000, 140,000, 150,000, 200,000, 250,000, 500,000, 1,000,000, 1,500,000, 2,000,000 centipoise or less. In some cases, the viscosity is between about 10 and 10,000 centipoise.

A cantharidin formulation can be free of or have a reduced level of Magnesium ions ($Mg^{2+}$) or reagents that can produce magnesium ions. A cantharidin formulation can be free of or have a reduced level of manganese ions ($Mn^{2+}$) or reagents that can produce manganese ions. A cantharidin formulation can be free of or have a reduced level of magnesium and manganese ions or reagents that can produce magnesium and manganese ions. $Mg^{2+}$ and/or $Mn^{2+}$ ions can interact with cantharidin, limiting its activity (e.g., therapeutic efficacy). A cantharidin formulation can comprise about 30, 20, 15, 10, 5, 4, 3, 2, 1, or about 0.1% magnesium ions. A cantharidin formulation can comprise about 30, 20, 15, 10, 5, 4, 3, 2, 1, 0.1% magnesium ions or less. A cantharidin formulation can comprise between about 0.1 and 1% magnesium ions. A cantharidin formulation can comprise less than about 0.1% magnesium ions. A cantharidin formulation can comprise between about 5 and 0.1% magnesium ions. A cantharidin formulation may comprise magnesium ions. A cantharidin formulation may not contain magnesium ions. A cantharidin formulation can be free or have a reduced level of manganese, calcium, sodium and potassium ions for similar reasons. For example, a cantharidin formulation can comprise about 30, 20, 15, 10, 5, 4, 3, 2, 1, or about 0.1% manganese ions. A cantharidin formulation can comprise about 30, 20, 15, 10, 5, 4, 3, 2, 1, 0.1% manganese ions or less. A cantharidin formulation can comprise between about 0.1 and 1% manganese ions. A cantharidin formulation can comprise less than about 0.1% manganese ions. A cantharidin formulation can comprise between about 5 and 0.1% manganese ions. A cantharidin formulation may comprise manganese ions. A cantharidin formulation may not contain manganese ions.

A cantharidin formulation of the present disclosure can contain other topical agents. Topical agents include, but are not limited to, local anesthetics, local analgesics, antimicrobial agents, microbicidal agents, disinfectants, antiseptics, antibiotics, bactericidal agents, bacteriostatic agents, cleansing agents, anti-inflammatory agents, anti-infective agents (e.g., gentian violet), emollients, astringents, anti-acne agents, anti-virals, anti-fungals, fungicides, anti-psoriasis agents, antiparasitics, steroid hormones such as corticosteroids. Examples of topical agents include, but are not limited to, Altabax (retapamulin), Amevive (alefacept), Avita gel, Bactroban cream, benzamycin, erythromycin, botox, cefazolin, dextrose, chloraprep (chlorhexidine gluconate), clindamycin phosphate, condylox (pokofilox), desonate (desonide), differin (adapalene), Dynabac, Elidel, Erivedge (vismodegib), Estrostep, norethindrone acetate, ethinyl estradiol, Extina (ketoconazole), Fiacea (azelaic acid), Finevin, Firazyr (icatibant), Gralise (gabapentin), Horizant (gapabentin enacarbil), hydrochloric acid, hydrogen peroxide, lamin, Invanz, lontocaine, IvyBlock, Klaron (sodium sulfacet amide), Lamisil (terbinafine hydrochloride), LaViv (azficel-T), Lustra, Luxiq (betamethasone valerate), Mentax (butenafine HCl), MetroLotion, Minoxidil, Noritate, nitric acid, Omnicef, Ortho Tri-Cyclee, norgestimate, Picato (ingenol mebutate), Propecia, Protopic (tacrolimus), Condylox (podophotoxin), Regranex (becaplermin), Renova, tratinoin, salagen, sandalwood oil, salicylic acid, Sklice (ivermectin), Stelara (ustkinumab), Sulfamylon, Sylatron (peg interferon alpha-2b), Tazorac, Teflaro (ceftaroline fosamil), Thalomid, Trichioroacetic acid, Tygacil (tigecycline), Veltin (clindamycin phosphate), tretinoin, Veregen (green tea sincatechins), Verdeso (desonide), Vibativ (telavancin), Vibativ (telavancin), Xyzal (levoctirizine dihydrochloride), Yervoy (ipilimumab), Zelboraf (vemurafenib), and Zyclara (imiquimod).

A cantharidin formulation can have the following components:

TABLE 1

Example cantharidin formulation

| Component | Amount (% weight/volume) |
|---|---|
| Ethanol | 0-99% |
| Acetone | 0-99% |
| Hydroxypropylcelluose | 0-10% |
| Nitrocellulose | 0-10% |
| Castor Oil | 0-5% |
| Camphor | 0-5% |
| Cantharidin | 0.001-7% |
| Denatonium Benzoate | 0.00001-1% |
| Gentian Violet | 0.00001-1% |

TABLE 2

An example of a cantharidin formulation that may be useful in treating heavily keratinized skin

| Component | Amount (% weight/volume) |
|---|---|
| Ethanol | 60.0% |
| Acetone | 13.0% |
| Salicylic Acid | 3.0% |
| Nitrocellulose | 1.0% |
| Castor Oil | 0.5% |
| Camphor | 0.5% |
| Cantharic acid | 1.0% |
| Trichloroacetic acid | 70.0% |
| Sodium lauryl sulfate | 1.0% |

TABLE 3

An example of a DMSO-based cantharidin formulation visible under ultraviolet (UV) light that may be useful in treating cosmetic lesion on the face of a subject

| Component | Amount (% weight/volume) |
|---|---|
| DMSO | 97.4% |
| Nitrocellulose | 1.0% |
| Castor Oil | 0.5% |
| Camphor | 0.5% |
| Cantharidin | 0.5% |
| Mag-indo-1 | 0.1% |

TABLE 4

Example of a low viscosity cantharidin formulation that may be useful in treating larger lesions

| Component | Amount (% weight/volume) |
|---|---|
| Ethanol | 49.25% |
| Acetone | 49.25% |
| Hydroxypropylcellulose | 0.0% |
| Nitrocellulose | 0.5% |
| Castor Oil | 0.0% |
| Camphor | 0.0% |
| Cantharidin | 1.0% |
| Denatonium Benzoate | 0.0% |
| Gentian Violet | 0.0% |

TABLE 5

Example of an easily visualized thick cantharidin formulation that may be useful where adhesion is a priority

| Component | Amount (% weight/volume) |
|---|---|
| Ethanol | 80.0% |
| Acetone | 8.9% |
| Hydroxypropylcellulose | 4.0% |
| Nitrocellulose | 4.0% |
| Castor Oil | 0.5% |
| Camphor | 0.0% |
| Cantharidin | 2.5% |
| Denatonium Benzoate | 0.0% |
| Gentian Violet | 0.1% |

TABLE 6

Example of a quick drying cantharidin formulation that may be useful as a chemical peel

| Component | Amount (% weight/volume) |
|---|---|
| Ethanol | 10.0% |
| Acetone | 89.5% |
| Hydroxypropylcellulose | 0.1% |
| Nitrocellulose | 0.1% |
| Castor OU | 0.1% |
| Camphor | 0.1% |
| Cantharidin | 0.1% |
| Denatonium Benzoate | 0.0% |
| Gentian Violet | 0.0001% |

TABLE 7

Example of a cantharidin formulation for the treatment of warts and molluscum

| Component | Amount (% weight/volume) |
|---|---|
| Ethanol | 70-90% |
| Acetone | 10-20% |
| Hydroxypropylcellulose | 0.2-4.0% |
| Nitrocellulose | 0.2-4.0% |
| Castor Oil | 0.1-1.0% |
| Camphor | 0.1-1.0% |
| Cantharidin | 0.1-1.0% |
| Denatonium Benzoate | 0.0001-0.1% |
| Gentian Violet | 0.0001-0.1% |

TABLE 8

Example of a cantharidin formulation

| Component | Amount (% weight/weight) |
|---|---|
| Ethanol | 25-35% |
| Acetone | 55-65% |
| Hydroxypropylcellulose | 0.1-2.0% |
| Nitrocellulose | 2.0-10% |
| Castor Oil | 0.5-2.0% |
| Camphor | 0.1-2.0% |
| Cantharidin | 0.1-1.2% |
| Denatonium Benzoate | 0.001-0.01% |
| Gentian Violet | 0.0001-0.001% |

TABLE 9

Example of a cantharidin formulation

| Component | Amount (% weight/weight) |
|---|---|
| Ethanol | 31.5% |
| Acetone | 60% |
| Hydroxypropylcellulose | 0.88% |
| Nitrocellulose | 4.5% |
| Castor Oil | 1.4% |
| Camphor | 0.92% |
| Cantharidin | 0.88% |
| Denatonium Benzoate | 0.006% |
| Gentian Violet | 0.0005% |

The cantharidin solutions described in Tables 7-9 can be prepared in the following manner. Acetone, ethanol and nitrocellulose are added to a glass vial to form a mixture. A polytetrafluoroethylene (PTFE) coated stir bar can be added and the mixture mixed until a homogenous viscous mixture is formed. Castor oil and camphor can be added to the mixture and stirred until homogenous. A 1% denatonium benzoate solution in ethanol can be added to the glass vial. A 1% gentian violet solution in ethanol can be added to the glass vial. Greater than 95% pure Cantharidin powder can be added to the glass vial. The mixture can be mixed until homogeneous. Hydroxypropylcellulose can be added and the mixture mixed until fully gelled and homogenous.

Another aspect of the present disclosure provides methods for delivering cantharidin formulations to subjects, which can be used to treat skin conditions, ailments and/or diseases, such as warts or cutaneous lesions. A method for treating a subject can comprise using an applicator device, system or kit of the disclosure to deliver a cantharidin formulation to a subject having or suspected of having a skin condition, ailment or disease, such as a wart.

Methods of the present disclosure include a user delivering a cantharidin formulation to a subject, or the subject delivering the cantharidin formulation to her or himself.

The subject can be diagnosed with a skin disease. The skin disease can cause an epithelial wart or other cutaneous lesion. The applicator device can be used to deliver the cantharidin formulations to the epithelial wart or cutaneous lesion. The delivery of the cantharidin formulation can remove the epithelial wart or cutaneous lesion from the subject.

After the cantharidin formulation is delivered to the subject, the epithelial wart can be removed from the subject within 1, 2, 3, 4, 5, 6, 7, 8, 9, 10, 11, 12, 13, or 14 days, weeks or months. The cantharidin formulation can be delivered to the subject at least 1, 2, 3, 4, 5, 6, 7, 8, 9, or 10 times a day, week or month.

The amount of cantharidin delivered to the subject in a single administration can be between about 0.001 mg to 100 mg, about 0.1 mg to 50 mg, about 0.1 mg to 10 mg, about 0.5 mg to 10 mg, about 0.5 mg to 5 mg, about 1 mg to 5 mg, or about 1 mg to 2 mg.

The cantharidin formulation delivered to the subject can comprise at least about 0.001% (weight/volume), 0.005%, 0.01%, 0.05%, 0.1%, 0.5%, 1%, 2%, 3%, 4%, 5%, 10%, 20%, 30%, 40%, or 50% of cantharidin. In some cases, the cantharidin formulation delivered to the subject comprises at most about 50% (w/v), 40%, 30%, 20%, or 10%, or 1% of cantharidin.

The cantharidin formulation delivered to the subject can comprise greater than or equal to about 50% (w/v), about 20% (w/v), about 10% (w/v), about 5% (w/v), about 1% (w/v), about 0.5% (w/v), or about 0.1% (w/v) of excipients.

A delivery device or system can be used to deliver a cantharidin formulation to a subject at a dose up to an including about 0.001 mg/day, 0.01 mg/day, 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 1.5 mg/day, 2 mg/day, 2.5 mg/day, 3.0 rag/day, 3.5 mg/day, 4.0 mg/day, 4.5 mg/day, 5.0 mg/day, 5.5 mg/day, 6.0 mg/day, 6.5 mg/day, 7.0 mg/day, 7.5 mg/day, 8.0 mg/day, 8.5 mg/day, 9.0 mg/day, 9.5 mg/day, 10.0 mg/day, 11 mg/day, 12 mg/day, 13 mg/day, 14 mg/day, 15 rag/day, 16 mg/day, 17 mg/day, 18 rag/day, 19 mg/day, or 20 mg/day. As an alternative, a delivery device or system can be used to deliver a cantharidin formulation to a subject at a dose of at least about 0.1 mg/day, 0.2 mg/day, 0.3 mg/day, 0.4 mg/day, 0.5 mg/day, 0.6 mg/day, 0.7 mg/day, 0.8 mg/day, 0.9 mg/day, 1 mg/day, 1.5 mg/day, 2 mg/day, 2.5 mg/day, 3.0 mg/day, 3.5 mg/day, 4.0 mg/day, 4.5 mg/day, 5.0 mg/day, 5.5 mg/day, 6.0 mg/day, 6.5 mg/day, 7.0 mg/day, 7.5 mg/day, 8.0 mg/day, 8.5 mg/day, 9.0 mg/day, 9.5 mg/day, 10.0 mg/day, 11 mg/day, 12 mg/day, 13 mg/day, 14 mg/day, 15 mg/day, 16 mg/day 17 mg/day, 18 mg/day, 19 ng/day, or 20 mg/day.

A delivery device or system of the present disclosure can be used to deliver a cantharidin formulation to a subject (e.g., to a skin area of the subject having or suspected of having a wart or cutaneous lesion) from once a day to once a month or more. As an alternative or in addition to, a delivery device or system of the present disclosure can be used to deliver a cantharidin formulation to a subject from once a day to once a week. As an alternative or in addition to, a delivery device or system of the present disclosure can be used to deliver a cantharidin formulation to a subject at least once a day, once every two days, once every three days, once every four days, once every five days, once every six days, once a week, once every 10 days, once every two weeks, once every three weeks, once a month, once every two months, once every three months, once every four months, once every five months, once every six months, once a year, or more. As an alternative or in addition to, a delivery device or system of the present disclosure can be used to deliver a cantharidin formulation to a subject at least once a day, or twice a day, or three times per day, or four times per day, or five times per day, or six times per day, or seven times per day, or eight times per day, or nine times per day, or ten times per day, or eleven times per day, or twelve times per day, or thirteen times per day, or fourteen times per day, or fifteen times per day, or sixteen times per day, or seventeen times per day, or eighteen times per day, or nineteen times per day, or twenty times per day, or twenty one times per day, or twenty two times per day, or twenty three times per day, or twenty four times per day. As an alternative or in addition to, a delivery device or system of the present disclosure can be used to deliver a cantharidin formulation to a subject as soon as skin begins to epithelialize after previous treatment. As an alternative or in addition to, a delivery device or system of the present disclosure can be used to deliver a cantharidin formulation to a subject as soon as skin has partially epithelized after previous treatment. As an alternative or in addition to, a delivery device or system of the present disclosure can be used to deliver a cantharidin formulation to a subject as soon as skin has fully epithelized after previous treatment.

A formulation, delivery device or system of the present disclosure can be used to deliver a cantharidin formulation to a subject's skin which was untreated, previously treated or to be further treated. Some examples of previous treatment include, but are not limited to, removal of scar tissue, scabs or keratinized tissue via debriding, scrubbing, soaking or surgical excision. Previous treatment can also include cryotherapy, cauterization, the application or acids or bases, application of salicylic acid, lasers, surgical debridement, soaking, hydrogen peroxide or immunotherapy. Previous treatment can also include the application tape, creams, ointments, solutions, waxes or hydrophobic barriers to limit the area of skin that is exposed to the cantharidin formulation. A cantharidin formulation can be used prior to or concurrent with surgical resection, cryotherapy, cauterization, the application or acids or bases, application of acids, lasers, surgical debridement, soaking, hydrogen peroxide, immunotherapy or covering the treated area with an occlusive tape or bandage.

A cantharidin formulation and associated delivery device or system can be used to treat the following; Acral fibrokeratoma, Acrodermatitus enterpathica, Acrokeratoelastoidosis, Actinic keratosis (solar keratoses), Adenoma sebaceum, Angiokeratoma, Atopic Dermatitis, Basal cell carcinoma, Benign fibrous histiocytomas, Bladder cancer. Bowen's disease. Breast cancer. Buschke-Ollendorff syndrome, Cervical cancer, Cervical dysplasia, Cherry angiomas, Chondrodermatitis nodularis chronica helicis, Cutaneous endometriosis. Cutaneous Leukemia. Cutaneous Lymphoma, Cutaneous meningioma, Cutaneous myxoma, Darier's disease. Dermal dendrocyte hamartoma, dermatofibroma, Dermatofibrosarcoma protuberans. Eccrine angiomatous hamartoma, Ectodermal dysplasia. Epidermal inclusion cysts, Epidermal Naevi (including but not limited to naevus sebaceous, Comedone naevus, Proteus syndrome-becker naevus), Epithelioid cell histiocytoma, Familial myxovascular fibromas. Fungal skin disease (including Lobomycosis), Granular cell tumor, Glucaonoma syndrome, Genital warts, Ichthyosis (including but not limited to Ichthyosis vulgaris, Ichthyosis lamellaria, X-linked Ichthyosis, epidermolytic hyperkeratosis, Ichthyosis acquista and keratosis palmoplantaris), Idiopathic guttate hypomelanosis, Infantile acropustulosis, Infantile fibromatosis, Kaposi's sarcoma, Keloid. Keratoacanthoma, Keratocyst, Knuckle pads, Lentigo, Melanoma, Microvenular hemangioma. Morton's neuroma, Multifocal lymphangioendotheliomatosis, Multinucleate cell angiohistocytoma, Multiple cutaneous leiomyomas, Mycosis fungoides, Neuroma cutis. Neurothekeoma, Nevus flammeus, Nevus lipomatosus superficialis, Pachydermodactyly, Palisaded encapsulated neuroma, Parasitic skin diseases (including but not limited to Scabies, Pediculosis, Tungiasis, Hookwork-related cutaneous larva migrans), Pityriasis ruba pilaris, Piloleiomyomas, Plexiform fibrohistiocytic tumor, Porokeratotic eccrine ostial and Dermal duct nevus, Progressive nodular histiocytoma Psoriasis (including but not limited to Psoriatic crytroderma, Palmoplantat psoriasis, Palmoplantar pustolosis, Generalized pustular psoriasis of Zumbusch, Lingua geographica), Porokeratosis, Seborrhoeic dermatitis, Seborrhoeic keratosis, Rhinophyma, Solitary cutaneous leiomyoma, Spider angioma, Targetoid hemosiderotic hemangioma, Squamous cell carcinoma, Tufted angioma, Venous lake, Urticaria pigmentosa, Xanthelasmoidal mastocytosis or Zosteriform metastasis.

Other skin ailments can also be treated with a cantharidin formulation including, without limitation, Benign epidermal cysts, Birthmarks, Calluses, Corns, Eczema, Freckles, Moles, Pigmentation disorders (Drug induced hyperpigmentation, Dyschromatosis symmetrica hereditaria, Dyschromatosis universalis hereditaria, Familial progressive hyperpigmentation, Galli-Galli disease, Hemosiderin hyperpigmentation, Idiopathic guttate hypomelanosis, Iron metallic discoloration, leukoderma, Melasma, Mukamel syndrome. Necklace of Venus, Nevus anemicus, Nevus depigmentosus, Pallister-Killian syndrome, Phylloid hypomelanosis, Piebaldism, Pigmentatio reticularis faciei et colli, Pilar Cysts, Pityriasis alba, Poikiloderma of Civatte, Poikiloderma vasculare atrophicans, Postinflammatory hyperpigmentation, Progressive macular hypomelanosis, Pruritus. Reticular pigmented anomaly of the flexures, Reticulate acropigmentation of Kitamura, Riehl melanosis, Shah-Waardenburg syndrome, Shiitake mushroom dermatitis, Tar melanosis, Titanium metallic discoloration, Transient neonatal pustular melanosis, Vagabond's leukomelanoderma, Vasospastic macules, Wende-Bauckus syndrome, X-linked reticulate pigmentary disorder, Yemenite deafblind hypopigmentation syndrome), Scars, Skin tags, Tattoo removal or Vitiligo (including but not limited to non-segmented Vitiligo, and/or Segmented vitiligo trichome vitiligo, Quadrichrome vitiligo, Vitiligo ponctué).

There may also be a use for a cantharidin formulation in epidermal skin rejuvenation, such as a skin peel or exfoliation, in individuals with sun damage or wrinkles.

Due to its chemotactic properties, ability to induce cell arrest and apoptosis, vesicant activity and other therapeutic outcomes a cantharidin formulation may have utility in combination with surgical, radiographic, immunotherapeutic, small molecule based, antibody-based, recombinant protein based, nucleic acid-based or chemotherapeutic agents. A cantharidin formulation may also have utility in as a second-line, third-line or forth-line therapeutic to treat patients who have failed prior therapies. Examples for use of cantharidin formulations, devices, and methods of the present disclosure include: immediately following Mohs Micrographic surgery in treating Basal Cell Carcinoma or after the failure of systemic chemotherapeutic agents in treating Mycosis fungoides or in combination with destructive therapies such as cryotherapy or hydrogen peroxide or acids or ingenol mebutate in the treatment of Actinic kerotisis or as a first line therapy in the treatment of Porokeratosis or Seborrheic keratosis.

A formulation, delivery device or system of the present disclosure can be used to treat warts, molluscum. Actinic keratosis. Seborrheic keratosis or other cutaneous hyperproliferative disorder that have failed or have been recalcitrant to prior therapy. Alternatively, a formulation, delivery device or system of the present disclosure can be used as a first-line therapy. Alternatively a formulation, delivery device or system of the present disclosure can be used in combination with another first line therapy.

A cantharidin formulation may be used to treat patients with cancer. For instance, a cantharidin formulation may be used to inhibit tumor growth and/or used to kill cancer cells directly. In some cases, a cantharidin formulation may be used to kill cancer stem cells. In some cases the cantharidin formulation may be used to treat benign cancerous lesions. For example, a cantharidin formulation may be used to kill cancer cells with a multi-drug resistant phenotype. In some situations, norcantharidin, cantharidimide, or norcantharimide or analogues of cantharidin may be utilized instead of cantharidin.

Cantharidin formulations, devices, systems, and methods can be used for other purposes, such as, for example, in the production of autologous or allogeneic skin that can used for skin grafts or as a blistering model for the testing of drugs or an approach for eliminating residual cancer cells following a surgical procedure.

Example

This example describes pharmacokinetic results from a Phase II clinical trial for the treatment of skin lesion resulting from *Molluscum contagiosum*. Patients received administrations of the cantharidin composition in Table 9 to *Molluscum contagiosum* lesions every 21 days for a maximum of 4 sessions or until complete clearance. Blood samples for systemic exposure evaluation were collected on Day 1, prior to the drug application, and 2 (±30 minutes), 6 (±1 hour) and 24 (±3 hours) hours post-application. The average age of the subjects was 7±3.5 years. The average body weight of the subjects was 58±34.6 lb. The average number of lesions per subject was 43.7±24.2.

Only one of the seventeen subjects had a plasma concentration of cantharidin above the lower limit of quantification (i.e., 2.5 ng/ml). The plasma concentration of cantharidin for all subjects was less than 3.3 ng/ml at all times sampled. Moreover, subjects (i) as young as 2 years old, (ii) having over 100 lesions, (iii) having genital lesions, and (iv) with as many as 2.26 lesions per lb had a plasma concentration of cantharidin below the lower limit of quantification. Table 10 shows the gender, age, weight, number of lesions, genital involvement, systemic exposure, lesions per pound of the subject, mg of composition used per treatment session, mg of composition per lesion, and mg of composition per pound of the subject for the subjects in the clinical trial.

TABLE 10

Subject Demographic and Pharmacokinetic Data

| Sex | Age (yr) | Wt. (lb) | No. of lesions | Genital involvement | Exposure (ng/ml) | Lesions/ lb | mg* (mg#) | mg*/ lesion (mg#/ lesion) | mg*/lb (mg#/lb) |
|-----|----------|----------|----------------|---------------------|------------------|-------------|-----------|---------------------------|-----------------|
| F | 6 | 47.1 | 45 | No | <2.5 | 0.96 | — | — | — |
| M | 13 | 88.4 | 22 | Yes | <2.5 | 0.25 | — | — | — |
| F | 9 | 68 | 27 | No | <2.5 | 0.40 | — | — | — |
| M | 8 | 58 | 32 | No | <2.5 | 0.55 | — | — | — |

TABLE 10-continued

Subject Demographic and Pharmacokinetic Data

| Sex | Age (yr) | Wt. (lb) | No. of lesions | Genital involvement | Exposure (ng/ml) | Lesions/lb | mg* (mg#) | mg*/lesion (mg#/lesion) | mg*/lb (mg#/lb) |
|---|---|---|---|---|---|---|---|---|---|
| M | 15 | 173 | 83 | No | <2.5 | 0.48 | — | — | — |
| F | 4 | 39 | 65 | No | <2.5 | 1.67 | — | — | — |
| M | 5 | 47 | 43 | No | <2.5 | 0.91 | — | — | — |
| M | 5 | 37 | 26 | No | <2.5 | 0.70 | 30 (0.26) | 1.2 (0.01) | 0.8 (0.01) |
| F | 4 | 34 | 47 | No | <2.5 | 1.38 | 160 (1.4) | 3.4 (0.03) | 4.7 (0.04) |
| M | 6 | 44 | 41 | No | <2.5 | 0.93 | 133 (1.17) | 3.2 (0.03) | 3.0 (0.03) |
| F | 8 | 50 | 29 | No | <2.5 | 0.58 | 136 (1.2) | 4.7 (0.04) | 2.7 (0.02) |
| M | 2 | 29.5 | 24 | No | 3.3 | 0.81 | 74 (0.65) | 3.1 (0.03) | 2.5 (0.02) |
| M | 8 | 65 | 29 | No | <2.5 | 0.45 | 85 (0.75) | 2.9 (0.03) | 1.3 (0.01) |
| F | 6 | 50 | 113 | Yes | <2.5 | 2.26 | 122 (1.07) | 1.1 (0.01) | 2.4 (0.02) |
| F | 6 | 43 | 30 | No | <2.5 | 0.70 | 108 (0.95) | 3.6 (0.03) | 2.5 (0.02) |
| M | 3 | 26 | 31 | No | <2.5 | 1.19 | 122 (1.07) | 3.9 (0.03) | 4.7 (0.04) |
| M | 11 | 87 | 56 | No | <2.5 | 0.64 | 167 (1.47) | 3.0 (0.03) | 1.9 (0.02) |

Mg* refers to milligrams of the composition.
Mg# refers to milligrams of cantharidin While certain embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A composition comprising:
   cantharidin, wherein the composition comprises greater than or equal to 0.7 and less than or equal to 0.9 weight per weight percent of cantharidin;
   acetone, wherein the composition comprises greater than or equal to 55 and less than or equal to 65 weight per weight percent of acetone;
   ethanol, wherein the composition comprises greater than or equal to 25 and less than or equal to 35 weight per weight percent of ethanol;
   castor oil, wherein the composition comprises greater than or equal to 1.2 and less than or equal to 1.6 weight per weight percent of castor oil;
   nitrocellulose, wherein the composition comprises greater than or equal to 3 and less than or equal to 6 weight per weight percent of nitrocellulose;
   hydroxypropyl cellulose, wherein the composition comprises greater than or equal to 0.5 and less than or equal to 1 weight per weight percent of hydroxypropyl cellulose; and
   camphor, wherein the composition comprises greater than or equal to 0.5 and less than or equal to 1.5 weight per weight percent of camphor.

2. The composition of claim 1 further comprising denatonium benzoate, wherein the composition comprises greater than or equal to 0.001 and less than or equal to 0.01 weight per weight percent of denatonium benzoate.

3. The composition of claim 1 further comprising gentian violet, wherein the composition comprises greater than or equal to 0.0001 and less than or equal to 0.001 weight per weight percent of gentian violet.

4. The composition of claim 1, wherein the composition comprises greater than or equal to 58 and less than or equal to 62 weight per weight percent of acetone.

5. The composition of claim 1, wherein the composition comprises greater than or equal to 28 and less than or equal to 32 weight per weight percent of ethanol.

6. The composition of claim 2, wherein the composition comprises greater than or equal to 0.004 and less than or equal to 0.008 weight per weight percent of denatonium benzoate.

7. The composition of claim 3, wherein the composition comprises greater than or equal to 0.0002 and less than or equal to 0.0008 weight per weight percent of gentian violet.

8. A single use applicator device comprising the composition of claim 1.

9. A method of treating a subject having a skin lesion comprising administering the composition of claim 1 to at least a portion of the skin lesion.

10. The method of claim 9, wherein the skin lesion is molluscum contagiosum.

11. The method of claim 9, wherein the skin lesion is seborrheic keratosis, actinic keratosis, milia, age spots, porokeratosis, or skin cancer.

12. The method of claim 9, wherein the skin lesion is a wart.

13. The method of claim 12, wherein the wart is a common wart, plantar wart, or genital wart.

14. The method of claim 9, wherein at least a portion of the composition remains on the skin lesion for greater than or equal to 12 hours and less than or equal to 48 hours.

15. The method of claim 9, wherein the plasma concentration of cantharidin in the subject is less than or equal to 3.3 ng/ml after at least 12 hours after the administration step.

16. The method of claim 9, wherein at least a portion of the composition remains on the skin lesion for up to 24 hours.

17. The composition of claim 1 further comprising:
    denatonium benzoate, wherein the composition comprises greater than or equal to 0.001 and less than or equal to 0.01 weight per weight percent of denatonium benzoate; and
    gentian violet, wherein the composition comprises greater than or equal to 0.0001 and less than or equal to 0.001 weight per weight percent of gentian violet.

18. The method of claim 12, wherein the wart is a common wart.

19. The method of claim 12, wherein the wart is a plantar wart.

20. The method of claim 12, wherein the wart is a genital wart.

* * * * *